(12) United States Patent  
Akagi

(10) Patent No.: US 7,039,155 B2
(45) Date of Patent: May 2, 2006

(54) MAMMOGRAPHIC SYSTEM AND APPARATUS

(75) Inventor: Eiichi Akagi, Hachioji (JP)

(73) Assignee: Konica Minolta Medical & Graphic, Inc., Tokyo (JP)

( * ) Notice: Subject to any disclaimer, the term of this patent is extended or adjusted under 35 U.S.C. 154(b) by 0 days.

(21) Appl. No.: 11/077,860

(22) Filed: Mar. 11, 2005

(65) Prior Publication Data

US 2005/0213702 A1 Sep. 29, 2005

(30) Foreign Application Priority Data

Mar. 25, 2004 (JP) ............................. 2004-089965

(51) Int. Cl.
*H05G 1/26* (2006.01)
(52) U.S. Cl. ......................................... 378/37; 378/165
(58) Field of Classification Search .................. 378/37, 378/116, 204, 207, 165, 115, 210
See application file for complete search history.

(56) References Cited

U.S. PATENT DOCUMENTS 6,379,044 B1 * 4/2002 Vastenaeken et al. ....... 378/207

* cited by examiner

Primary Examiner—David V. Bruce
Assistant Examiner—Hoon Song
(74) Attorney, Agent, or Firm—Lucas & Mercanti LLP

(57) ABSTRACT

A mammographic apparatus comprises an identification information reader and the identification information reader transmits the cassette identification information read by the identification information reader together with the radiography execution information to the control apparatus, in the control apparatus, it becomes possible to automatically correlate the radiographic order information and the radiography execution information based on the cassette ID (identification information). Accordingly, since the radiologist can eliminate the selection work to select of the radiographic order information for correlating the radiography execution information prior to the radiography, the efficiency of radiographic work can be improved. In the case of mammography which conducts a plurality of radiographs with different radiographic body parts with different radiographic directions, since the selection operation can be eliminated, the radiologist does not need to move the control apparatus for a selection operation and especially, the efficiency of radiographic work can be improved.

15 Claims, 19 Drawing Sheets

FIG. 9

| | RADIOGRAPHIC ORDER INFORMATION | | | | | | | | | | |
|---|---|---|---|---|---|---|---|---|---|---|---|
| | PATIENT INFORMATION | | | | RADIOGRAPHY INFORMATION | | | | RADIOGRAPHY EXECUTION INFORMATION | | |
| ORDER ID | PATIENT ID | NAME | AGE | ..... | RADIOGRAPHIC PORTION DIRECTION | RADIOGRAPHY DATE | ..... | CASSETTE ID | RADIOGRAPHIC PORTION DIRECTION | TUBE VOLTAGE (kV) | PRESSURE (mm) |
| 0001 | 1001 | HANAKO YAMADA | 40 | ..... | LEFT UP TO DOWN | 2003/4/1 | ..... | 1010101 | | | |
| 0002 | 1001 | HANAKO YAMADA | 40 | ..... | LEFT INSIDE TO OUTSIDE | 2003/4/1 | ..... | 1010102 | LEFT INSIDE TO OUTSIDE | 60 | 10 |
| 0003 | 1001 | HANAKO YAMADA | 40 | ..... | RIGHT UP TO DOWN | 2003/4/1 | ..... | 1010103 | | | |
| 0004 | 1001 | HANAKO YAMADA | 40 | ..... | RIGHT INSIDE TO OUTSIDE | 2003/4/1 | ..... | 1010104 | | | |
| 0005 | 2050 | KYOKO SUZUKI | 40 | ..... | LEFT UP TO DOWN | 2003/4/1 | ..... | — | | | |
| ..... | ..... | ..... | ..... | ..... | ..... | ..... | ..... | ..... | ..... | ..... | ..... |

MAMMOGRAPHIC SYSTEM AND APPARATUS

FIELD OF THE INVENTION

The present invention relates to a mammographic system and a mammographic apparatus for taking mammographs or radiographs of breast images.

BACKGROUND OF THE INVENTION

An image obtained by using X-rays is widely used for a medical image of a diagnosis. In recent years, the medical image has been digitalized. For example, CR (Computed Radiography) apparatus is an apparatus which allows a phosphor plate on which a stimulable phosphor layer is formed absorbs X-rays passing through an object, scans the phosphor plate by laser beams to stimulate X-ray energy stored in the phosphor layer to radiate phosphor rays and obtains image signals after converting the phosphor rays to electric signals by using light-electric conversion.

In a conventional method, when taking a radiograph of a patient, a radiologist records radiography execution information such as the amount of x-rays applied to the patient and the direction of radiograph of the patient on a recording sheet. After that a supervisor gathers the recording sheet and controls the radiography execution information in database which is formed by inputting the radiography execution information into HIS (Hospital Information System) controlling information in a hospital or RIS (Radiology Information System) controlling information in a radiology for each patient. However, according to these controlling methods, the radiologist has to record the radiography execution information in the recording paper every time when conduction radiography and input the radiography execution information into HIS. The workflow was complicated and may be troublesome.

In recent years, utilized is a radiography system for simplifying the workload of a radiography management system by connecting the radiographic apparatus to a control apparatus for controlling the operation of the radiographic apparatus, obtaining the radiography execution information from the radiographic apparatus and uploading it into HIS through a network. This is disclosed in Japanese Patent Application Open to Public Inspection No. 2003-8815.

This radiographic system utilizing stimulable phosphor has two types of systems. One is a dedicated system including a phosphor plate (not portable) utilized for both taking a radiograph and reading out the image on the phosphor plate. The other is a cassette type system including a portable cassette with a phosphor plate therein capable of transporting. Here, the radiography of the cassette type system will be described by referring to FIG. 19.

As shown in FIG. 19, a cassette type mammographic system comprises a radiographic apparatus for taking radiographs of the medical images of a patient by using cassette, a reading apparatus for reading the medical image from the cassette and a control apparatus for controlling the reading apparatus to obtain read medial images. The control apparatus is arranged so that it can communicate with HIS or RIS.

In the mammographic system configured as described above, radiographic information, such as patient information, the name of a patient who is going to be an object and sexuality of the patient, and radiographic order information, such as a radiographic body part of the patient and the method of radiography, etc., are issued by HIS/RIS based on a medical doctor order prior to taking radiographs and delivered to the control apparatus. In the control apparatus, when taking radiographs, order information is displayed as a list to do.

The workflow of the radiography in the radiographic system will be described.

1) The radiologist selects radiographic order information for a patient from the list of the radiographic order information displayed in the control apparatus. The selection of the radiographic order information may be conducted prior to the radiography.

2) The radiologist conducts a work called cassette registration to clarify the relationship between the cassette to be used for the radiograph and the radiographic order information. In the cassette to be used, cassette ID is provided to identify the cassette among a plurality of cassettes. The radiologist inputs the cassette ID corresponding to the selected radiographic order information to the control apparatus in the process of the registration work. In the control apparatus, the selected radiographic order information is displayed and the selected photographic order information and the inputted cassette ID are correlated. The cassette ID registration may be conducted after finishing the radiography. A method to register the cassette ID prior to the radiography is called pre-registration and a method to register the cassette ID after the radiography is called after-registration.

3) The radiologist takes radiographs by the radiographic apparatus after confirming the patient to be an object and the radiographic body part of the patient using displayed radiographic order information. In the radiographic apparatus, once X-rays is irradiated and a radiographic image is recorded onto the cassette, radiography execution information is transmitted to the control apparatus.

4) The radiologist sets the cassette in a reading apparatus for reading the cassette. In the reading apparatus, the medical images and the cassette ID are read and the read medical images and the cassette ID are transmitted to the control apparatus after correlating the read medical images and the cassette ID.

5) In the control apparatus, the selected radiographic order information and the radiography execution information are correlated. The medical image transmitted from the reading apparatus has been correlated to the radiographic order information based on the cassette ID. As a result, the medical images, the radiographic order information and the radiography execution information are correlated each other and transmitted to HIS or RIS as additional information of the medical image.

However, according to the method described above, the radiologist has to select the radiographic order information corresponding to the radiography execution information and the selection work is complicated. Especially, in the case of mammography, even for a patient, a plurality of radiographies with different radiographic body parts combined with different radiographic directions, such as MLO-L (medio lateral oblique-left breast), MLO-R (right breast), CC-L, (cranio caudal-left breast) and CC-R (right breast) is common. In such a case, the radiologist has to move to the reading apparatus to set the cassette into the reading apparatus, then come back to the control apparatus to select the radiographic information and move to the radiographic apparatus. The work efficiency is not good.

SUMMARY OF THE INVENTION

An object of the present invention is to improve the efficiency of radiographic work of mammographs by automating the correlation work of mammographs, radiographic order information and the radiography execution information.

According to one aspect of the present invention, a mammographic system comprises at least a mammographic apparatus for taking a mammograph of a patient by irradiating X-rays onto the breast and for recording the mammograph onto a medium in a cassette, a reading apparatus for reading the mammograph out of the cassette, and at least a control apparatus for obtaining the mammograph, the control apparatus being connected with the mammographic apparatus and the reading apparatus, the mammographic apparatus having an identification information reader for reading a cassette identification information of the cassette used for taking the mammograph and a communication section for transmitting radiography execution information including the cassette identification information which has been read by the identification information device, wherein the control apparatus comprises a memory section for storing radiographic order information, an input section for inputting the cassette identification information used for taking the mammograph, and a controlling section for correlating the cassette identification information inputted by the input section with the radiographic order information and storing in the memory section, and correlating the radiography execution information with radiographic order information based on the cassette identification information included in the radiography executing information transmitted from the mammographic apparatus and the cassette identification information included in the radiographic order information which has been stored in the memory section.

According to one aspect of the present invention described above, since a mammographic apparatus comprises an identification information reader and the identification information reader transmits the cassette identification information read by the identification information reader together with the radiography execution information to the control apparatus, in the control apparatus, it becomes possible to automatically correlate the radiographic order information and the radiography execution information based on the cassette ID (identification information). Accordingly, since the radiologist can eliminate the selection work to select of the radiographic order information for correlating the radiography execution information prior to the radiography, the efficiency of radiographic work can be improved. In the case of mammography which conducts a plurality of radiographs with different radiographic body parts with different radiographic directions, since the selection operation can be eliminated, the radiologist does not need to move the control apparatus for a selection operation and especially, the efficiency of radiographic work can be improved.

According to the another aspect of the present invention, even a plurality of reading apparatuses and a plurality of control apparatuses are set, the radiographic order information and the radiography execution information are correlated to the mammographs which are obtained from each reading apparatus based on the cassette ID information.

According to another aspect of the present invention, a mammographic system comprises a mammographic apparatus for taking a mammograph of a patient by irradiating X-rays onto a breast and for recording the mammograph onto a medium in a cassette, a reading apparatus for reading the mammograph out of the cassette, and a control apparatus for obtaining the mammograph which has been read out of the cassette, wherein the mammographic apparatus comprises a first identification information reader for reading an cassette identification information to be used for taking the mammograph, an information generating device for generating radiography execution information including key information which correlates the radiography execution information with radiographic order information, and a first communication section for transmitting the radiography execution information including the key information generated by the information generating device every time when taking the mammograph and the cassette identification information which has been read by the identification information reader, wherein the reading apparatus comprises a second identification information reader for reading the cassette identification information when the mammograph is read out of the cassette, and a second communication section for transmitting the mammograph and the cassette identification read by the second identification information reader information to the control apparatus, wherein the control apparatus comprises a memory section for storing the radiographic order information including the key information, and a controlling section for correlating the radiography execution information and the cassette identification information received with the radiography execution information with the radiographic order information based on the key information included in the radiography execution information transmitted from the mammographic apparatus and the key information included in the radiographic order information stored in the memory section, and correlating the mammograph with the radiographic order information based on the cassette identification information correlated with the radiographic order information and the cassette identification information transmitted from the reading apparatus with the mammograph.

According to the another aspect of the present invention described above, since a mammographic apparatus comprises an identification information reader and the identification information reader transmits the radiography execution information including the identification information and key information of a cassette read by the identification information reader to the control apparatus, in the control apparatus, it becomes possible to correlate the radiographic order information and the radiography execution information based on the key information, and also correlate the mammographs to the radiographic order information based on the cassette ID information. Namely, it becomes possible to correlate the mammographs, radiographic order information and the radiography execution information. Accordingly, since the radiologist can eliminate the selection work to select of the radiographic order information for correlating the radiography execution information prior to the radiography, the efficiency of radiographic work can be improved. In the case of mammography which conducts a plurality of radiographies with different radiographic body parts with different radiographic directions, since the selection operation can be eliminated, the radiologist does not need to move the control apparatus for a selection operation every time when taking radiographs for a selecting work, and especially, the efficiency of radiographic work can be improved. Further, since it is not necessary to register cassettes to be used for the radiography in the control apparatus, it becomes possible to eliminate the registration work of the radiologist and miscorrelation over the plurality of radiographies. Also, since the cassette does not need to be specified by the specific radiographic body part and radiographic direction, the efficiency of the radiographic work can be achieved.

According to the another aspect of the present invention, since a mammographic apparatus comprises a reader for reading cassette ID information, the control apparatus of the mammographic system becomes possible to automatically correlate radiographic order information to the cassette ID information based on the cassette ID information by transmitting the cassette ID information together with the radiography execution information to the controller of the mammographic apparatus.

BRIEF DESCRIPTION OF THE DRAWING

FIG. 9 shows a data configuration of order file 361

DETAIL DESCRIPTION OF THE EMBODIMENTS

The First Embodiment

In the first embodiment of the present invention, an example for correlating cassette ID information with mammographs, radiographic order information and the radiography execution information based on cassette ID information in a control apparatus in this embodiment, an ID information reader for reading the cassette ID information of a cassette used when taking radiographs, is provided in a mammographic apparatus and read cassette ID information is transmitted to the control apparatus.

Firstly, the configuration of the present invention will be explained.

Figure 1:
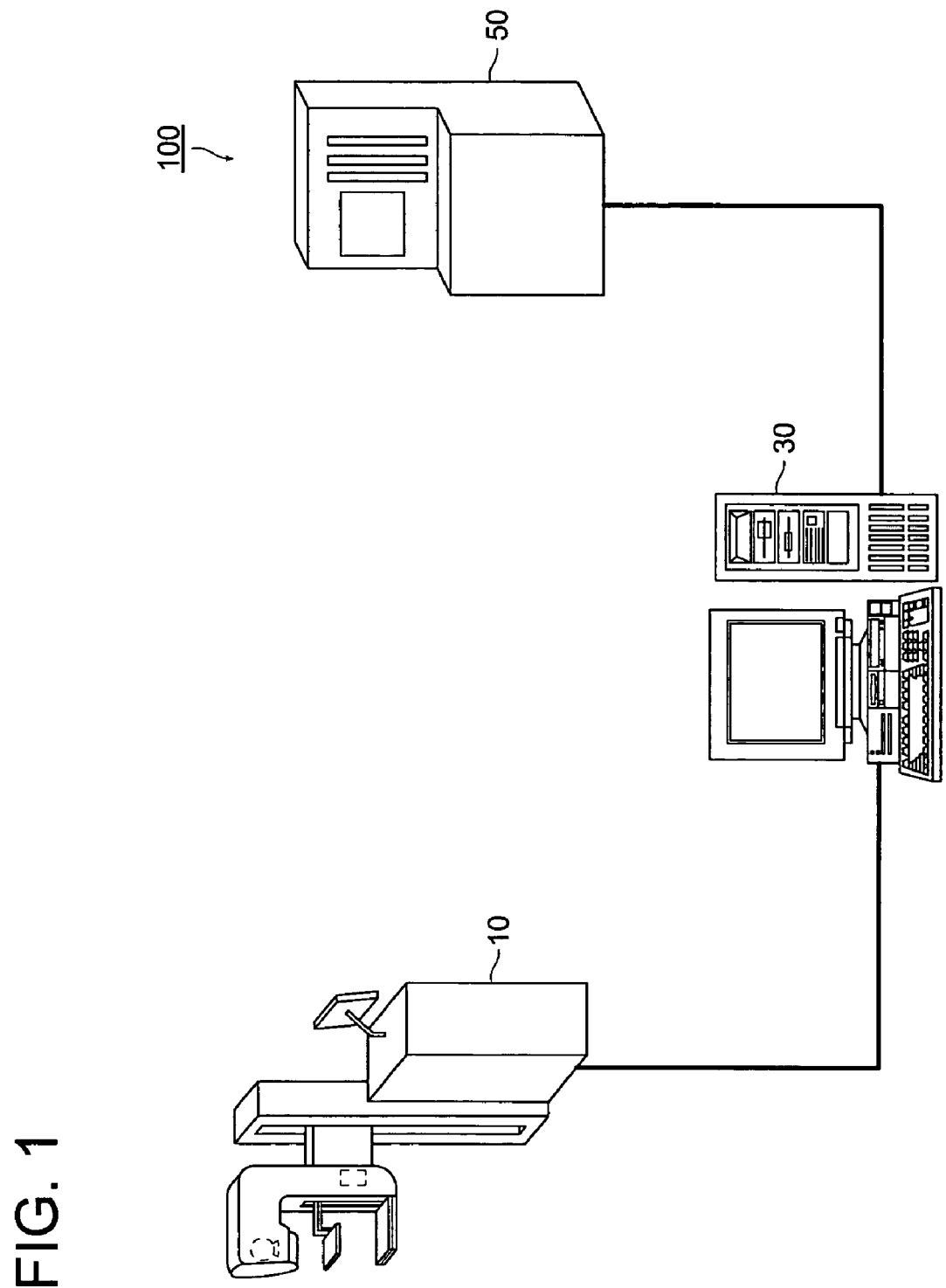
FIG. 1 is a system configuration of mammographic system 100 being an embodiment of the present invention.

FIG. 1 is a system configuration of mammographic system 100 being an embodiment of the present invention. As shown in FIG. 1, mammographic system 100 comprises mammographic apparatus 10, control apparatus 30 and reading apparatus 50. Mammographic apparatus 10 and reading apparatus 50 are connected to control apparatus 30 so that information transmission and receiving are available each other.

Mammographic apparatus 10 is an apparatus for irradiating X-rays against a patient breast as an object to radiograph the breast. In this embodiment, a mammographic apparatus in which a cassette is used for radiography will be described.

Figure 2:
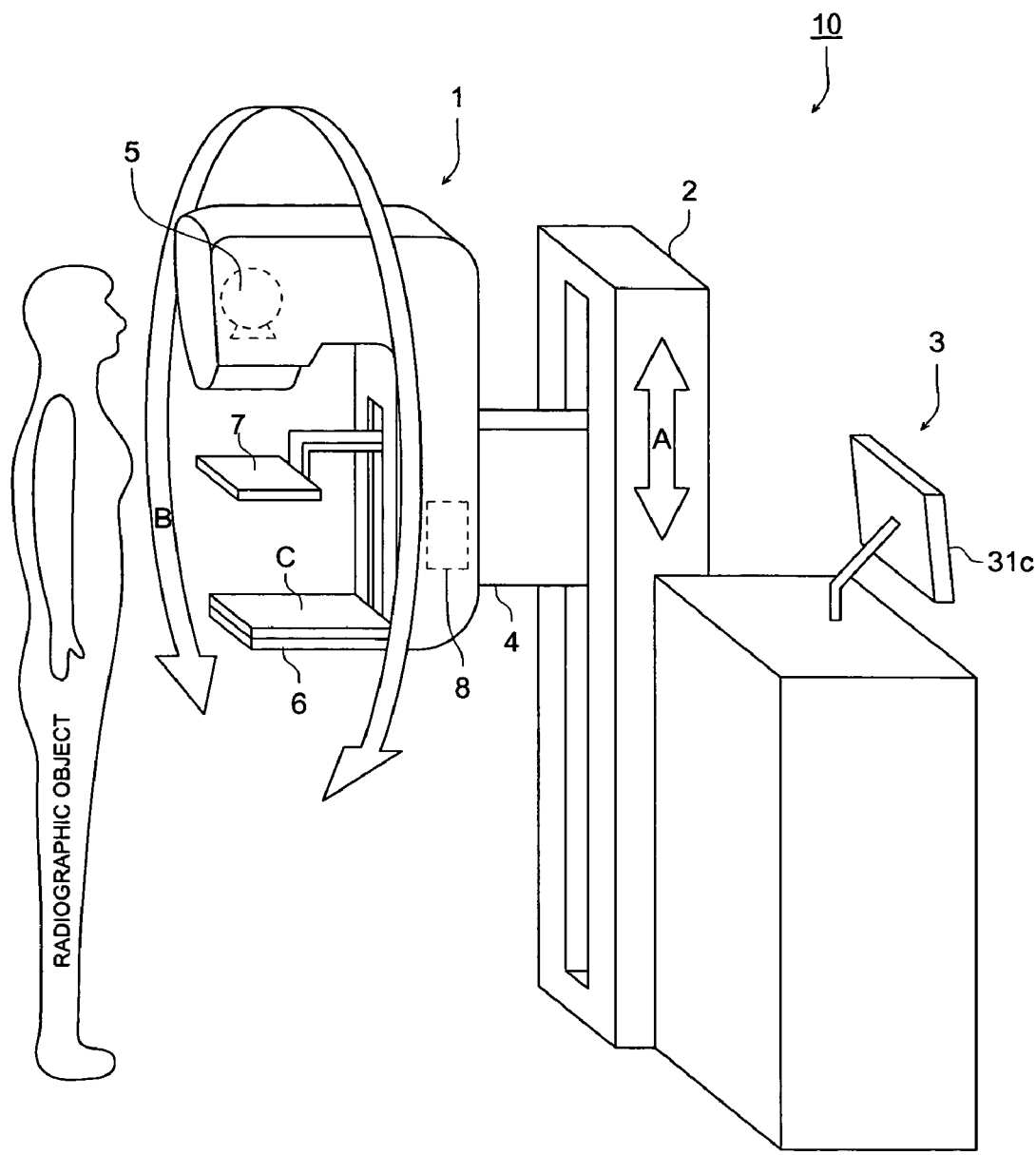
FIG. 2 is an external view of mammographic apparatus 10.

In FIG. 2, mammographic apparatus 10 is shown.

As shown in FIG. 2, mammographic apparatus 10 comprises radiographic section 1 for irradiating X-rays for radiography, support column 2 and main body 3. Radiographic section 1 is structured so that the height of radiographic section 1 is adjustable along support column 2 (in the direction shown in an arrow) according to the height of the breast of the patient. Further radiographic section 1 is structured so that radiographic section 1 is capable of rotating on supporting shaft 4 for changing the radiographic direction in the direction shown in an arrow B. Main body 1 can be not only manually rotated by a radiologist but also rotated under the control of main body with which the radiologist operates.

Figure 3:
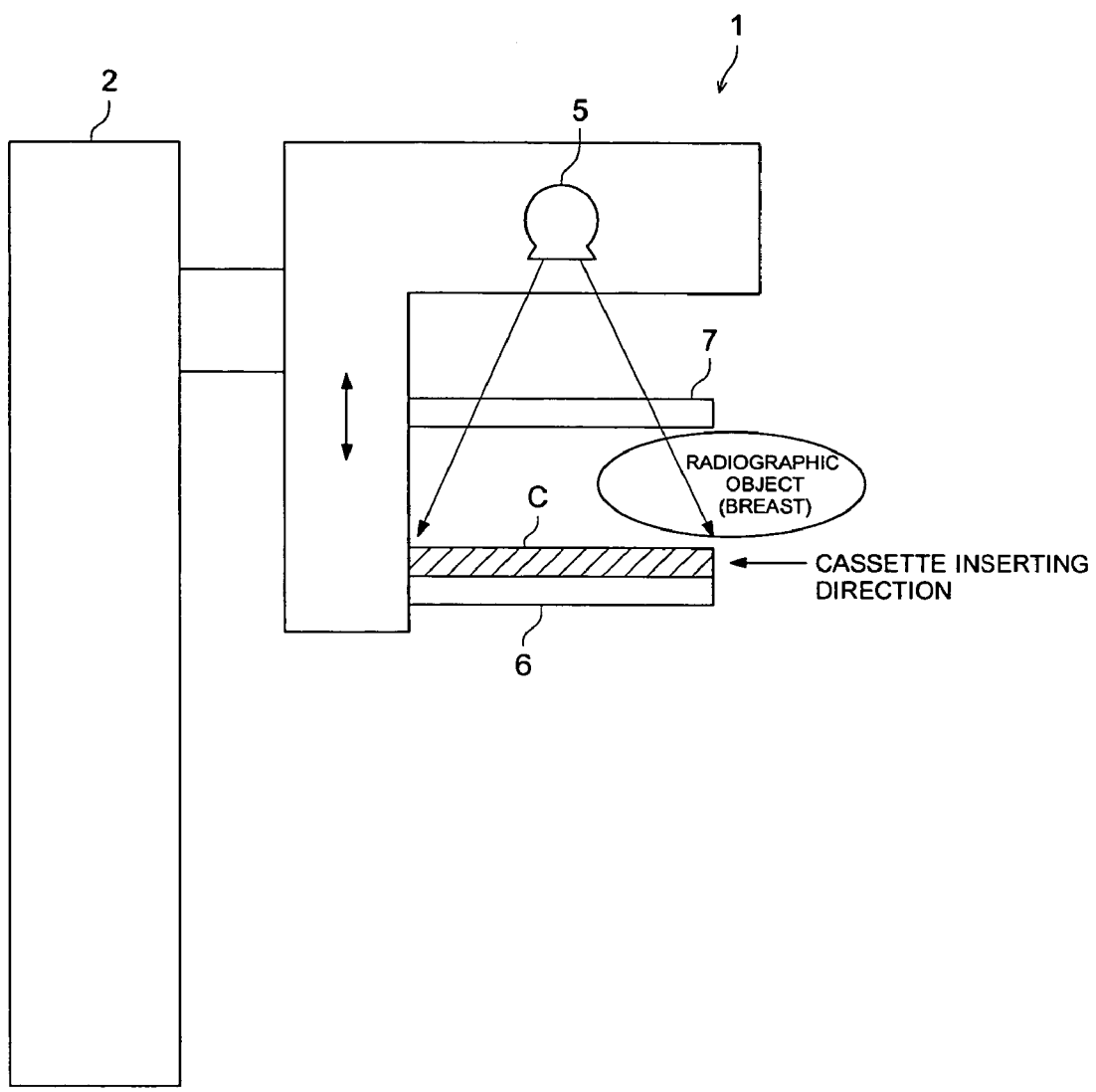
FIG. 3 is a side view of radiographic section 1 with radiographic table 6 on which cassette C is set.

In radiographic section 1, X-ray source 5 for generating X-rays and radiographic table 6 to put a breast of the patient thereon are oppositely provided and pressing board 7 for sandwiching the breast placed on radiographic table 6 to press the breast is arranged. A side view of radiography is shown in FIG. 3. As shown in FIG. 3, radiographic section 1 is structured so that cassette C can be set on radiographic table 6 and a cassette holder (not shown) for holding cassette C is provided on radiographic table 6. Cassette C contains a phosphor plate for absorbing X-rays passing through an object for recording an X-ray image. As a cassette, it is preferable that the cassette is a dedicated cassette just for mammography and the cassette is structured so that one side of the cassette radiographs the object as much closer as possible to the chest walls of the patient.

Figure 4:
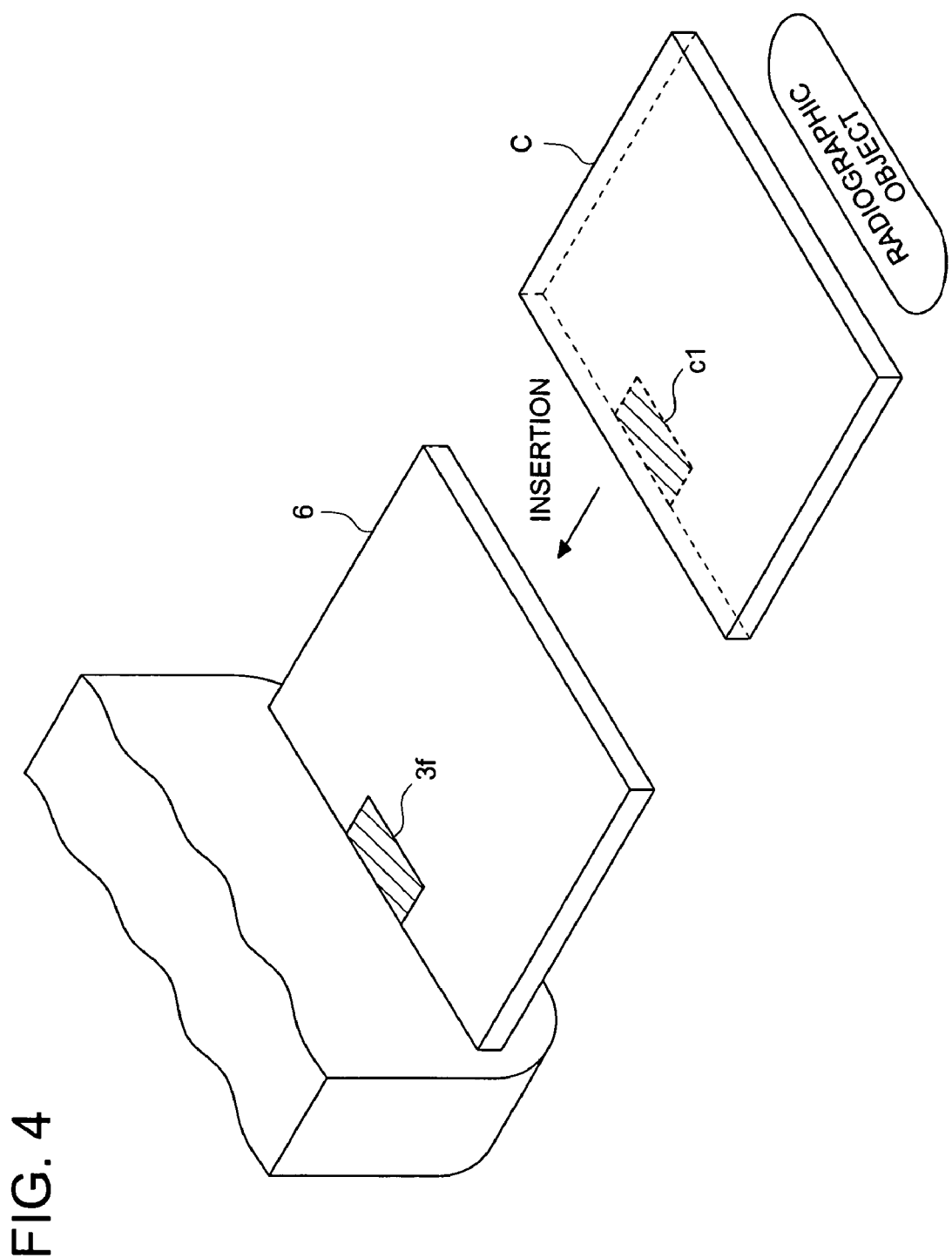
FIG. 4 shows radiographic table 6 provided with ID reader 3f and cassette C provided with ID section C1.

FIG. 4 is a perspective view of radiographic table 6 and cassette C to be set on radiographic table 6.

As shown in FIG. 4, ID section C1 on which a bar cords for showing ID is displayed is provided on cassette C. On the other hand, ID reader 3f for reading the bar cords displayed on ID section C1 of cassette C is provided in radiographic table 6. ID section C1 of cassette C is provided on the rear side of the recording surface of an X-ray image. Namely, it is provided on the surface facing to radiographic table 6 and the center of one side which is positioned on the depth side in the cassette inserting direction not to be duplicated with the object. ID reader 3f in radiographic table 6 is provided on the surface on which cassette C is set and in the center of the side which is opposed to the object.

The position of ID section C1 and ID reader 3f is not limited to the position shown in FIG. 4 if the both positions are identical when cassette C is set on radiographic table 6.

The display method of cassette ID in ID section C1 may be a bar code label on which bar cords are printed.

Figure 5:
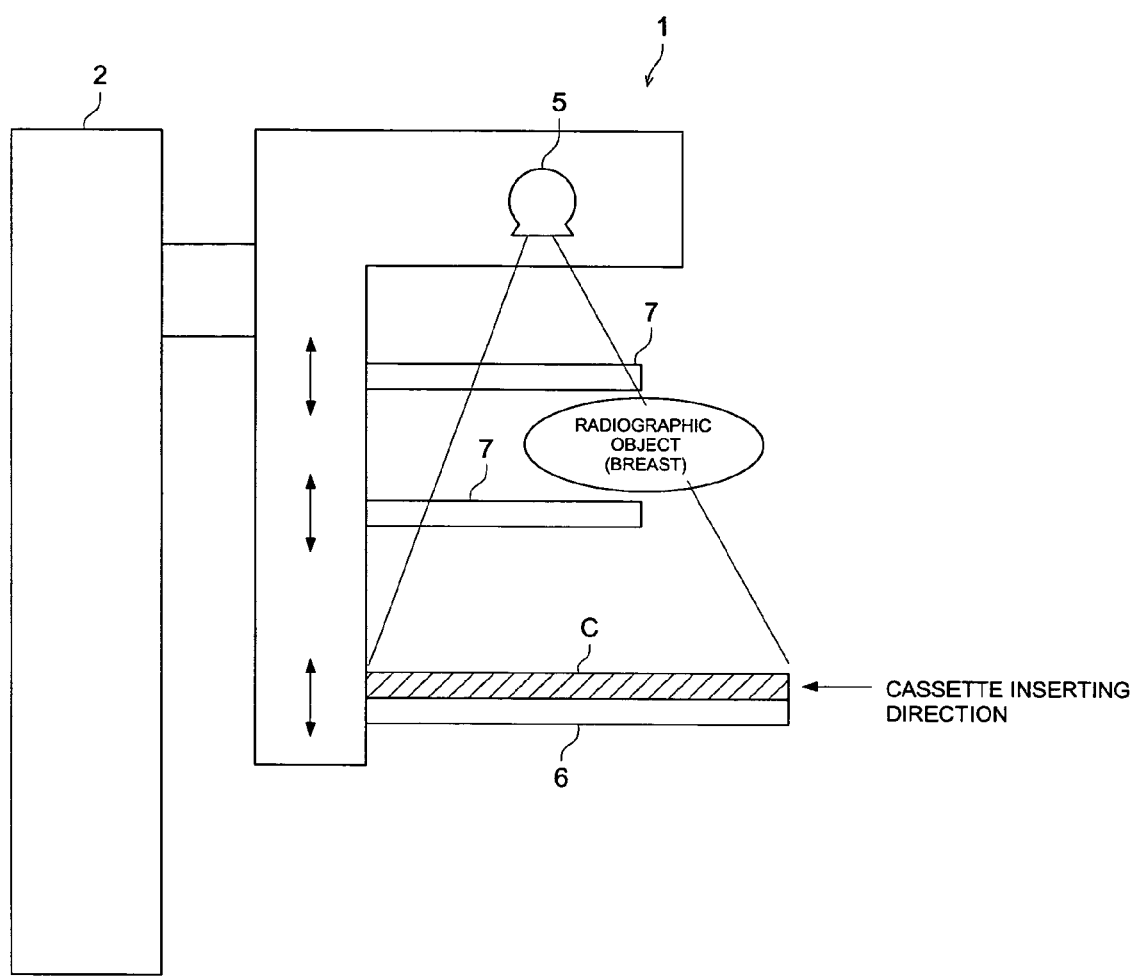
FIG. 5 is a side view of radiographic section 1 to which phase contrast radiography is applied.

Further, when phase contrast radiography, radiographic section 1 is structured as shown in FIG. 5. As shown in FIG. 5, radiographic section 1 comprises two pieces of pressure boards 7 and radiographic table 6 under pressure boards 7. Two pieces of pressure boards 7 and radiographic table 6 are structured so that they can independently move up and down. The height of pressure tables 7 and radiographic table 6 can be adjusted according to the height of the object. In the case of phase contrast radiography, since the size of a cassette is larger than the cassette used for normal radiography, (in normal radiography, 8×10 inch size cassette is used, in phase contrast radiography, 14×17 inch cassette is used in magnification factor of 1.7) the size of radiographic table 6 is expanded.

In the radiographic section 1, angle detecting section 8 for detecting the rotating angle which the radiographic section 1 rotes on supporting shaft 4 as a rotary shaft is provided. Angle detecting section 8 transmits the detected angle to main section 3 when taking radiographs.

The internal configuration of main section 3 will be described by referring to FIG. 6.

Figure 6:
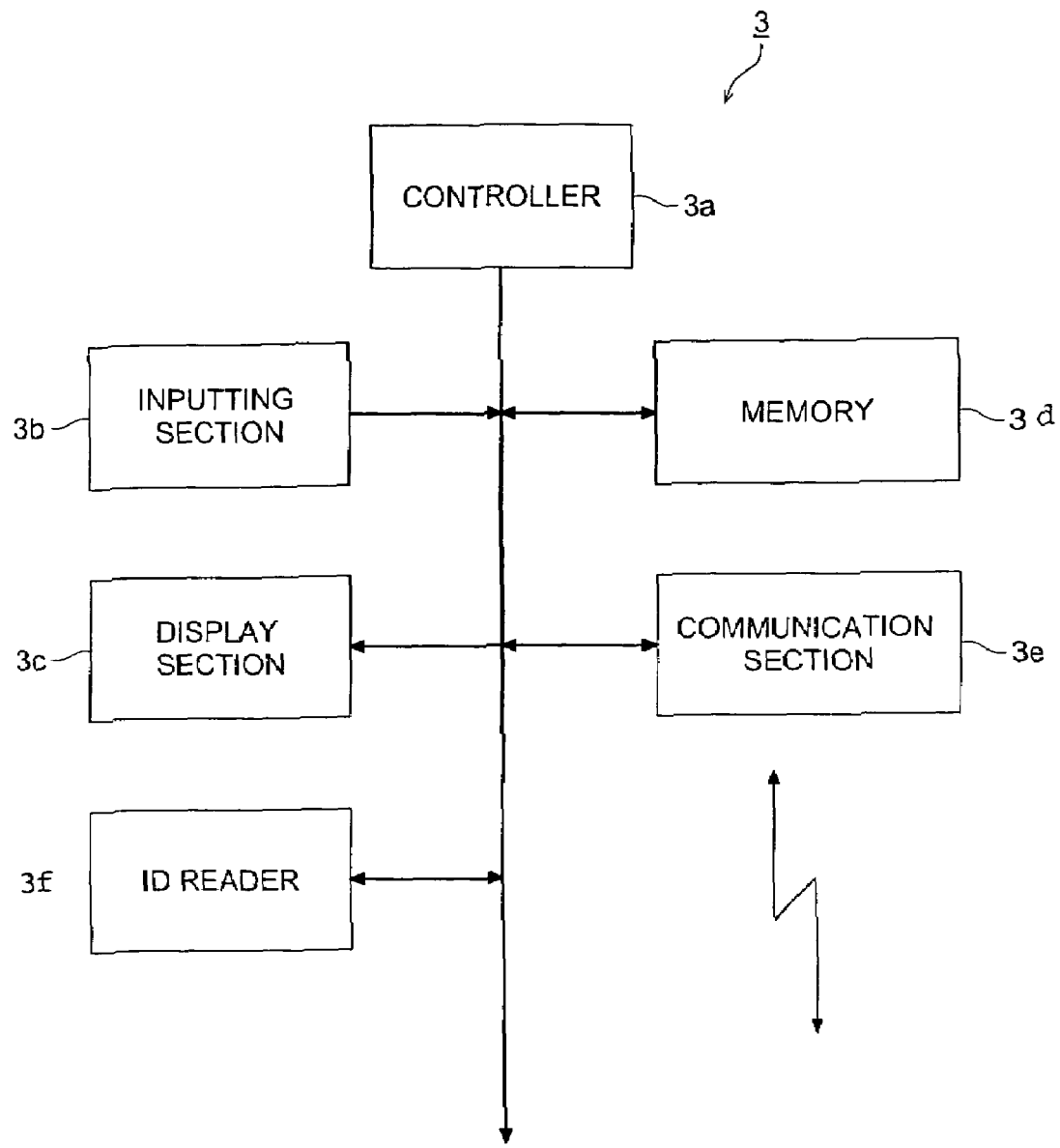
FIG. 6 is a functional block diagram main section 3.

As shown in FIG. 6, main section 3 comprises controller 3a, input section 3b, display section 3c, memory 3d, communication section 3e and ID reader 3f.

Controller 3a comprises CPU (Central Processing Unit) and works with a first radiation process program read from memory 3d to generally control an X-ray irradiation timing and an adjustment of an irradiation amount of X-ray source 5, the rotation control of radiographic section 1 and radiography operation of each section in mammographic apparatus 10. Controller 3a determines a radiography portion and the radiography direction (it will be called a body part direction, hereinafter) based on the rotation angle information when the rotation angle of radiographic section 1 from angle detecting section 8 is inputted to controller 3a.

Figure 7:
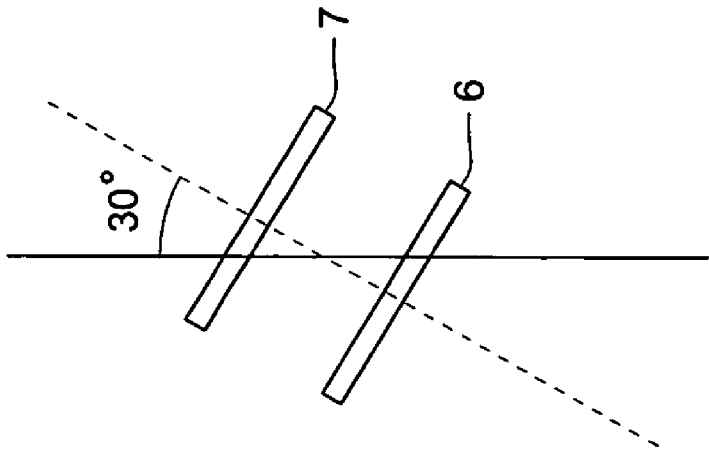
FIG. 7 shows an example for explaining how to determine the radiographic body part and the radiographic direction from the rotation angle information of main section I.
Figure 7:
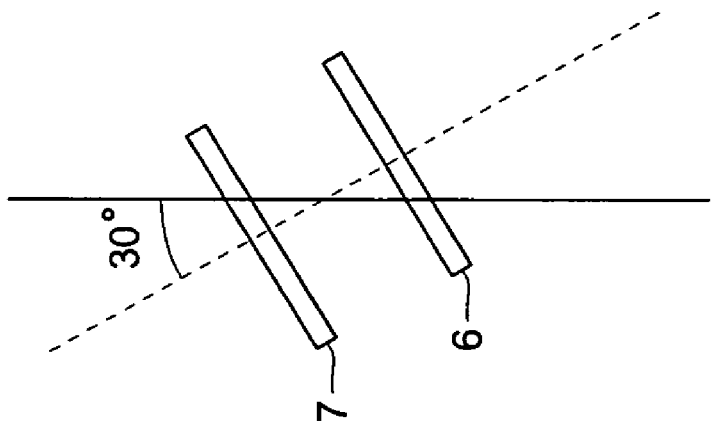

An example of determination of the body part direction will be described by referring to FIG. 7. FIGS. 7(a) and 7(b) are drawings showing pressure board 7 and radiography-board 6 viewed from an object side. As shown in FIGS. 7(a) and 7(b), assuming that the normal position where radiographic section 1 does not rotate is set to 0 degree, and radiography section rotates in the counter clockwise by 30 degree to take a radiograph of a left breast with oblique presentation, the detected rotation angle is "−30 degree". As shown in FIG. 7(b), in a case that in order to take a radiograph of a right breast with oblique presentation, the radiography section is rotated in clockwise by 30 degree, the rotation angle "+30 degree" is detected. Namely, it is determined that when the detected angle falls "+", the radiographic body part is a right breast and the detected angle falls "−", the radiographic body part is a left breast. And when the rotation angle is between 0 and 15 degree, the radiographic direction is an up to down direction (CC), and when the rotation angle is between 15 degree and 75 degree, it is an oblique presentation, and when the rotation angle is between 75 degree and 90 degree, it is determined as an inside to outside direction.

In the first radiographic process, controller 3a generates execution result in radiographic section 1 after the radiography such as, for example, tube-voltage (unit; kV) of X-ray source 5, tube-current (unit; mA) value, X-ray irradiating amount (multiply the tube-current value and irradiating time (second)), pressure of pressure board 7 (a moving distance of pressure board 7, unit; mm), a body part direction (shown by a character code. The first code shows a radiographic body part, R; a right breast, L; a left breast, and the second code shows a radiographic direction, CC; an up to down direction, M; an inside to outside direction and MLO; medio lateral oblique presentation) as radiography execution information. And, controller 3a allows control apparatus 30 to contain cassette ID information (bar code data) read by ID reader 3f when taking radiographs, to the generated radiography execution information and to transmit them to control apparatus 30 through communication section 3e.

Input section 3b comprises keys for inputting various radiography conditions and outputs operation signals corresponding to key operations to controller 3a. For example, numeric keys for inputting the tube voltage, the tube current value and rotational angle value of radiographic section 1 and various keys are provided.

Still, radiographic body part keys for inputting the radiographic body part of the radiography, for example, whether it was a left breast or a right breast in CC radiography and/or radiographic direction keys for inputting the rotation angle of radiographic section 1 may be provided. The radiographic direction keys comprise an up to down (CC) direction key, an inside to outside direction key and an oblique direction key which correspond various radiographic directions. For example, when the inside to outside direction key is pushed, radiographic section 1 is automatically rotated to the inside to outside direction for the radiography. When these radiographic direction keys are provide, the radiographic direction specified by the pushed key is included by converting "+" or "−" to "a right breast" or "a left breast" in the radiography execution information.

Display section 3c comprises display 31c including LCD (Liquid Crystal Display) as shown in FIG. 2 and displays various display information, such as input information from input section 3b and processed results by controller 3a on display 31c.

Memory 3d comprises RAM (Random Access Memory) and ROM (Read Only Memory) and stores various programs of the first radiographic process of the present invention and/or a radiographic program of mammographs. Memory 3d also temporally stores the processed results by controller 3a and stores various information such as the radiography execution information.

Communication section 3e comprises a network interface card (it will be described NIC hereinafter; Network Interface Card) or communication interface such as MODEM. Namely, a communication means is achieved by transmitting the radiography execution information including cassette ID information to control apparatus 30 after the radiography by communication section 3e.

ID reader 3f is an identification information reader for reading cassette ID. ID reader 3f comprises a bar code scanner. When a radiologist starts procedure for taking radiographs, ID reader 3f automatically starts reading cassette ID. Practically, ID reader 3f executes light-scanning of the ID section C1 of cassette C set on radiographic table 6 to read bar cords displayed in ID section C1 and outputs data to controller 3a. In this embodiment, the cassette ID is read by using bar cords. However, the present invention is not limited to this embodiment. For example, a radio IC tag storing the cassette ID data may be adhered on the cassette ID and ID reader 3f may be a system capable of reading stored ID data in the IC tag or other reading systems.

Next, control apparatus 30 will be described.

Figure 8:
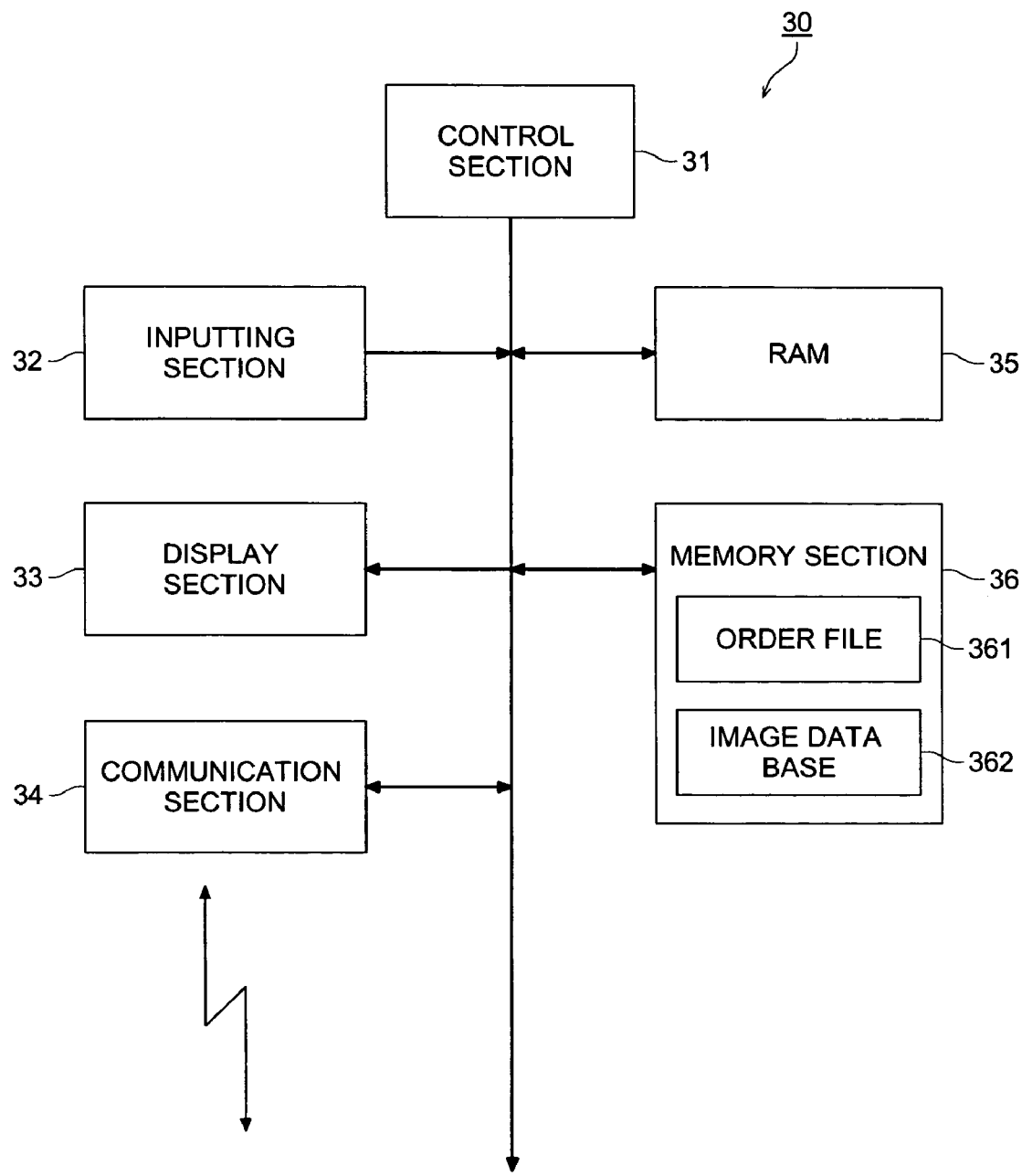
FIG. 8 is a functional block diagram of control apparatus 30.

FIG. 8 shows a functional block diagram of control apparatus 30.

As shown in FIG. 8, control apparatus 30 comprises control section 31, input section 32, display section 33, communication section 34, RAM 35 and memory section 36.

Control section 31 comprises CPU, etc., and installs the first radiographic process program (refer to FIG. 10), etc. and a system program stored in memory 36 into RAM 35 to totally control a process operation under the co-work of these programs.

In the first radiographic process program, prior to radiography, radiographic order information is selected. When cassette ID is inputted, the cassette ID is correlated to the radiographic order information and stored in order file 361. This is called cassette registration. After the radiography, when the first radiographic process program receives radiography execution information from mammographic apparatus 10, it correlates the information related the radiography to the radiographic order information based on the cassette ID contained in the received radiography execution information and cassette ID contained in the radiographic order information of the selected patient and stored it in order file 361. When mammographs and cassette ID correlated to mammographs from reading apparatus 50 are received, radiographic order information and radiography execution information are correlated to the mammographs based on the cassette ID and the mammographs are stored in image DB 362. This is called image registration. Namely, control means is established by correlating mammographs, radiographic order information and radiography execution information each other in control section 31.

Input section 32 comprises numeric keys, character keys, a keyboard including various functional keys and a touch panel structured into one body together with display section 33 and outputs operation signals corresponding to operated keys to control section 31. Namely, inputting means can be realized by inputting cassette, ID by operating input section 32. It also may be possible that by providing a bar code reader with control apparatus 30, cassette ID may be inputted by reading cassette ID C1 by the bad code reader.

Display section 34 comprises LCD and/or CRT (Cathode Ray Tube) for displaying the list of the radiographic order information, mammographs, various operation screens or confirmation screen to confirm the relationship between the radiographic order information and the radiography execution information and various display information, such as processed results by control section 31.

Communication section 34 comprises NIC and MODEM, etc, for transmitting and receiving information between external equipment. For example, prior to radiography, communication section 34 receives radiographic order information from HIS and/or RIS (not shown) and after the radiography, receives radiography execution information from mammographic apparatus 10. And communication section 34 also receives mammographs and cassette ID correlated to mammographs from reading apparatus 50.

RAM 35 forms a work area for temporally storing various programs executed by control section 31 and data associated with these programs.

Memory section 36 comprises magnetic or optical medium or semiconductor memory for storing the first radiographic process program and data processed in each program other than a system program.

Memory section 36 is a memory means for memorizing radiographic order information including key information and including order file 361 capable of memorizing and updating the radiographic order information. As shown in FIG. 9, order file 361 stores the radiographic order information based on identification information (it will be called order ID hereinafter) for independently identifying radiographic order information. The radiographic order information includes a patient ID of a patient to be an object, patient information, such as a patient name (it will be called patient information hereinafter), a body part direction and radiography execution information including date of the radiography (it will be called radiographic information hereinafter). Cassette ID of a cassette used for radiography based on radiographic order information and radiography execution information are correlated to radiographic order information.

Reading apparatus 50 will be described.

Reading apparatus 50 is designed for reading mammographs recorded in cassette C. Reading apparatus 50 comprises a image reading device for reading mammographs by irradiating excited light beams to a phosphor plate of set cassette C and photo-electrically converting the photo-stimulated light beams, an identification information reader for reading cassette ID shown in ID section C1 of cassette C and a communication device (not shown), such as NIC and/or MODEM. Reading apparatus 50 reads out medical images and cassette ID based on the control of control apparatus 30 and the read medical images to which the cassette ID is correlated is transmitted to control apparatus 40.

Next, the operation of mammographic system 100 will be described. The first radiographic process conducted in mammographic system 100 will be explained by referring to FIG. 10. As a base for the explanation, in this embodiment, it is assumed that since when taking radiographs of breast images, there is no case that the same radiograph is taken with the same portion direction, when a plurality of terms of radiographic order information is registered for a patient, each body part direction has a different body part direction from each other.

Figure 10:
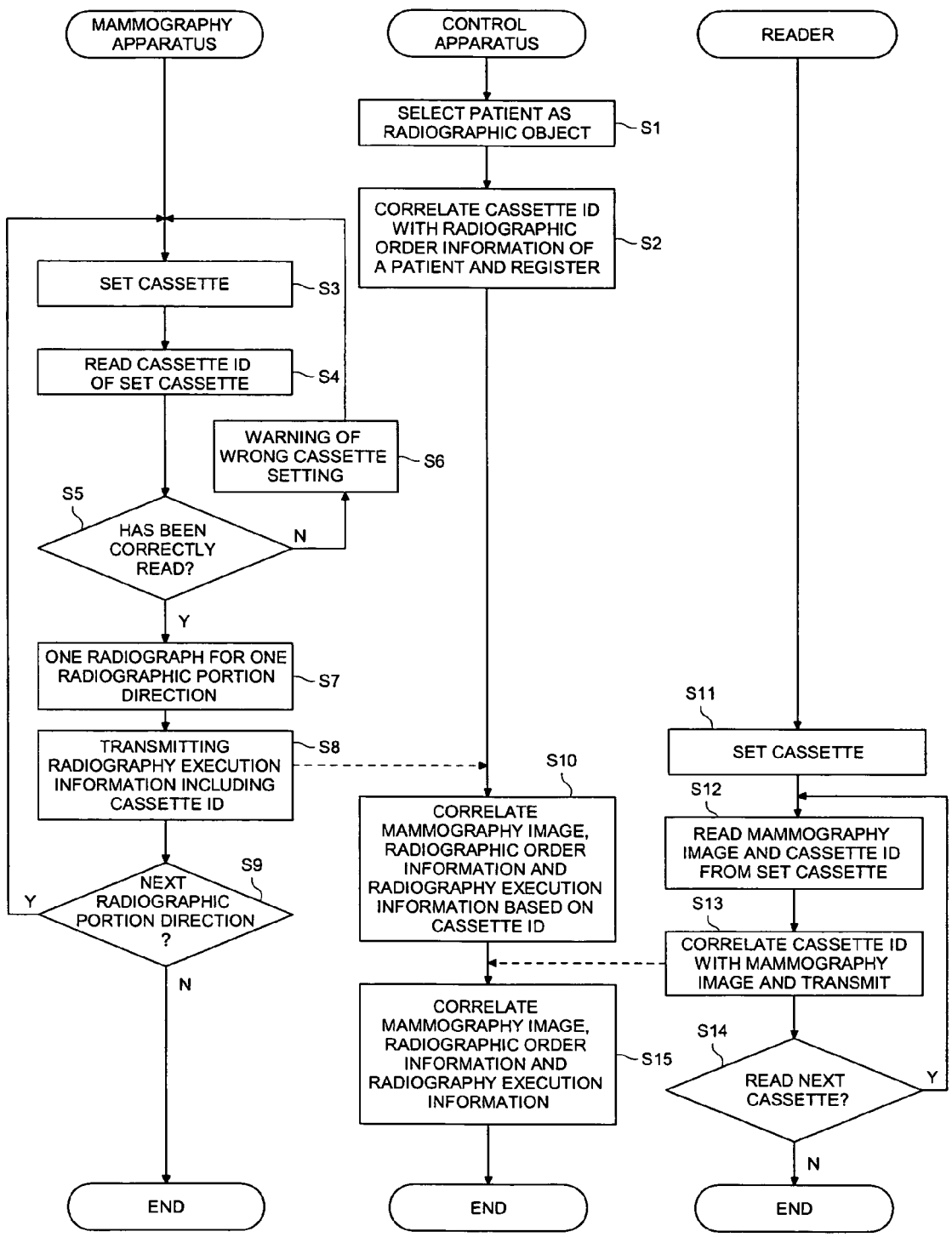
FIG. 10 is a flowchart describing the first radiographic process executed in mammographic system 100.

In the first radiographic process shown in FIG. 10, the list of patients to be radiographed is displayed in display section 33 of control apparatus 30 based on the radiographic order information stored in order file 361. When a radiologist selects and inputs a patient to be radiographed among the patient listed and displayed on the display section 33, then the list of the radiographic order information corresponding to the selected patients to be radiographed is displayed in control apparatus 30 (step S1).

Then, the cassette registration of a cassette to be used for the radiography for a selected patient is conducted (step 2). When a radiologist inputs cassette ID of a cassette to be used for the radiography through input section 32 to control apparatus 30, inputted cassette ID is correlated to the radiographic order information displayed on the top of the list in control apparatus 30 and stored into order file 361. Here, it is assumed that for a selected patient, a left breast and a right breast with an up to down direction and an inside to outside direction for each breast, total four terms of radiographic order information that corresponds to four cassette registrations are registered.

Then, the radiologist moves to a radiography room where mammographic apparatus 10 is set, with a plurality of cassettes C with which cassette registration has been done and sets cassette C which has been registered based on radiographic order information, on radiographic table 6 of mammographic apparatus 10. The radiologist makes the patient being a radiographic object stand on a radiography position, and inputs a radiography start signal through input section 3b after adjusting the radiography portion and the radiography direction for radiography. In mammographic apparatus 10, cassette C has been set and the a radiography start signal have been inputted (step S3), cassette ID of cassette C which has been set is read (step S4). Then, in ID reader 3f, it is determines whether cassette ID is correctly read (step S5).

Figure 11:
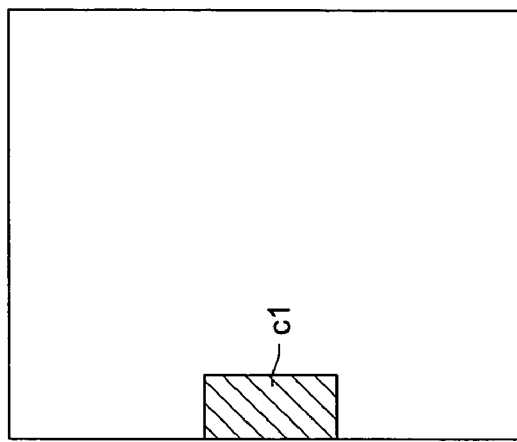
FIG. 11(a) shows correct insertion example of cassette C.
FIGS. 11(b) and 11(c) show wrong insertion examples of cassette C.
Figure 11:
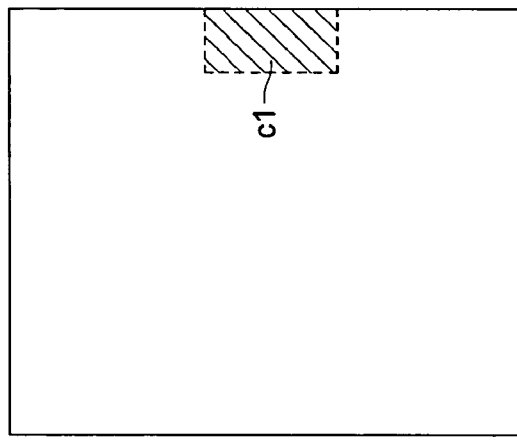
Figure 11:
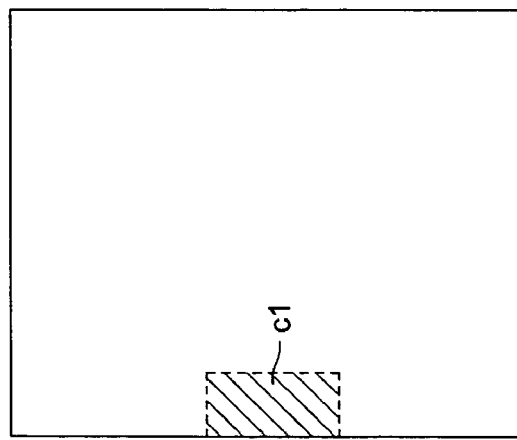

As shown in FIG. 4, since ID reader 3f is provided in a depth side in the inserting direction, when ID section C1 is set in the surface facing to radiographic table 6 as shown in FIG. 11(a) and ID section C1 is put in the depth side in the inserting direction, ID reader correctly reads ID section C1. However, as shown in FIG. 11(b), when cassette C is reversibly inserted so that cassette ID section C1 is positions in the entrance side in the inserting direction; as shown in FIG. 11(c), when the cassette surface is reversibly inserted (upside down); or when cassette C is not fully inserted and not correctly inserted (not shown), since the readable area of ID reader 3f does not coincide with the position of ID section C1 of cassette C, reading of cassette ID is not correctly conducted.

Accordingly, when cassette C is wrongly inserted and ID reader 3f do not correctly read cassette ID (step S5; N), message announcing a read-error of cassette ID is displayed on display 3c, and warning that cassette C has been wrongly inserted (step S6). After the warning, the process returns to step S3 and insertion of cassette C is conducted again.

On the other hand, when cassette c is correctly inserted and cassette ID is correctly read by ID reader 3f (step S5; Y), in mammographic apparatus 10, X-rays are irradiated according to the radiography direction inputted from input section 3b and radiography is conducted. Namely, in one body part direction, one radiograph is taken (step S7). After the radiography, in mammographic apparatus 10, radiography execution information including cassette ID read by ID reader 3f is generated and transmitted to control apparatus 30 (step S8).

When all radiographs for one patient have not been taken and following body part direction is scheduled (step S9; Y); in mammographic apparatus 10, the process is returned to step S3; cassette C used for following radiography is set; and the radiography operation described above is repeated (step S3–S8). When all radiographs are taken (step S9; N), this process finishes.

In control apparatus 30 where the radiography execution information including cassette ID information from mammographic apparatus 10 is received, based on the received cassette ID and registered cassette ID which is correlated to radiographic order information of a selected patient, the radiography execution information is correlated to the radiographic order information and memorized in order file 361 (step S10).

Figure 12:
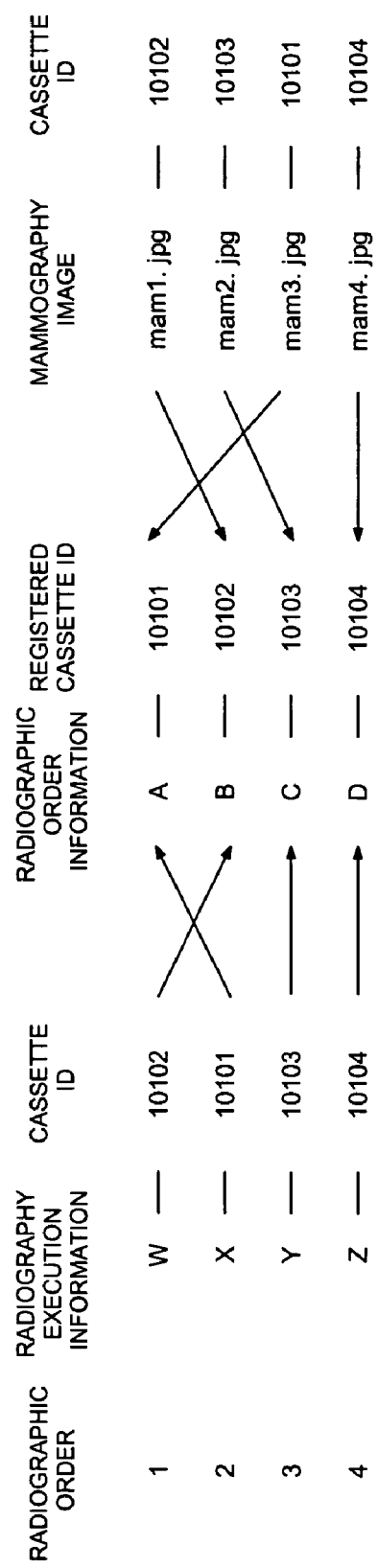
FIG. 12 shows a correlation between a mammograph and radiographic order information and the radiography execution information.

For example, as shown in FIG. 12, assuming that there are radiographic order information from A to D for a selected one patient and cassette registrations have been done for each radiographic order information from A to D, when radiography is conducted with the order of cassette 10102, 10101, 10.103 and 10104, radiography execution information W-Z which include each cassette ID information used in each radiography operation in the order of the radiography is transmitted to control apparatus 30. In control apparatus 30, since cassette ID 10101 is correlated with radiographic order information A, cassette ID 10102 corresponding with radiographic order information B, cassette ID 10103 corresponding with radiographic order information C and cassette ID 10104 corresponding with radiographic order information D, radiographic order information B is correlated with radiographic conduct information W; radiographic order information A is correlated with radiographic conduct information X; radiographic order information C is correlated with radiographic conduct information Y; and radiographic order information D is correlated with radiographic conduct information Z so that cassette ID coincides with each other.

On the other hand, the radiologist carrying all cassette C used for the radiography moves to reading apparatus 50, sets one of cassette C into reading apparatus 50 and inputs reading instruction after finishing a plurality of radiographies for a patient. In reading apparatus 50, when cassette C is set (step S11), mammographs and cassette ID are read from the set cassette C (step S12) and cassette ID is correlated with the mammograph by writing the read cassette ID in a header area of the image data of mammograph. The mammograph with which a cassette ID is correlated is transmitted to control apparatus 30 from reading apparatus 50 in the order by which the mammograph is read (step 13).

When reading all cassettes C(s) for one patient has not finished and there is a next cassette to be read (step S14; Y), in reading apparatus 50, the process is returned to the process of steps S11–S13 and repeats the reading operations of next cassette C being set. When reading all cassettes C has finished (step S14; N), this process finishes.

In control apparatus 30, when a mammograph is received from reading apparatus 50, it is stored into image database 362 and correlated with radiographic order information and radiography execution information based on cassette ID corresponding to the mammograph and cassette ID corresponding to radiographic order information (step S15). The radiographic order information and the radiography execution information correlated to the mammography are attached to the mammograph as additional information.

As shown in an example in FIG. 12, when cassette ID 10102 is correlated with mammograph data file mam1.jpg, cassette ID 103 is correlated with mammograph mam2.jpg and cassette ID 10104 is correlated with mammograph mam4.jpg, radiographic order information B and radiography execution information W are correlated with mammograph mam1.jpg, radiographic order information C and radiography execution information Y are correlated with mammograph mam2.jpg, radiographic order information A and radiography execution information X are correlated with mammograph mam3.jpg and radiographic order information D and radiography execution information Z are correlated with mammograph mam4.jpg.

A radiologist returns to control apparatus 30 to operate it after finishing the read operation of cassette C with reading apparatus 50. When finishing the correlation operation of the mammograph, radiographic order information and radiography execution information in control apparatus 30, a confirmation screen for confirming the correlation between mammograph and radiographic order information and radiography execution information is displayed in display 33 and finishing the process.

The radiologist moves for taking radiographs of the next patient after confirming the correlation by the confirmation screen. In mammographic system 100, the first radiographic process described above is repeated again from step S1.

As described above, providing ID reader 3f for reading cassette ID in mammographic apparatus 10 and transmitting the read cassette ID together with radiography execution information to control apparatus 30 allow control apparatus 30 to automatically correlate a mammograph with radiographic order and radiography execution information based on cassette ID. Accordingly, the selection operation for selecting radiographic order information with which radiographic order information is correlated by the radiologist prior to the radiography can be eliminated and the efficiency of radiographic work can be improved.

When taking radiographs of breast images, since it is common to take a radiograph or a plurality of radiographs of each left and right breast with an up-down direction, an inside-outside direction and an oblique direction, at least not less than two radiographs per a patient are obtained. Accordingly, registering all cassettes to be used for a patient prior to the radiography makes it possible to continuously take a plurality of radiographs for the patient and to reduce the workload of the radiologist because the radiologist can complete the radiography with only one movement to a control apparatus, a mammographic apparatus and a reading apparatus.

Since the correlation is obtained by using cassette ID, the radiologist does not need to memorize which cassette has taken radiograph with which body part direction and it reduces radiologist workload.

In mammographic apparatus 10, since radiographic table 6 is structured into one configuration together with ID reader 3f and ID section C1 of cassette C is automatically read, the radiologist does not need to input cassette ID and it is not only convenient but also can prevent the radiologist from conducting a human error of the radiologist such as oblivion of inputting cassette ID. When cassette C has not been correctly set and the cassette ID cannot be correctly read, the warning is displayed. Accordingly, cassette miss-reading can be prevented and miss-radiography based on wrong setting of cassette C can also be prevented.

The description of the first embodiment is an preferable embodiment of mammographic system 100 to which the present invention is applied and not limited to this embodiment.

For example, according to the description above, a continuous workflow, which conducts registrations of a plurality of cassettes for a plurality of radiographs for a patient is described. However, the present invention is not limited to this but it may be a workflow, which conduct registrations of a cassette for a radiography. In this case, in every radiography, a mammograph, radiographic order information and radiography execution information are correlated based on cassette ID in control apparatus 30 same as the description above.

In the description above, an example in which cassette registration is conducted prior to the radiography is described. However, it may be done after the radiography. In the latter case, after selecting a patient to be a radiographic object, taking radiographs with mammographic apparatus 10 without conducting the cassette registration, then cassette registration of cassette C, which is used with radiographic order information of a patient who has been selected in control apparatus 30, is conducted after finishing image reading in reading apparatus 50. In control apparatus 30, a mammograph, radiographic order information and radiography execution information are correlated each other based on the registered cassette ID, and the mammograph and cassette ID read by reading apparatus 50.

Although it is desirable that with regard to read timing of the cassette ID in ID reader 3f, since it can warn Of a reading error and can be made to reset with cassette C before photography, when it is not able to correctly read the cassette C before photography, as mentioned above, it may be read after the radiography. In either case, from the viewpoint for raising the certainty of cassette ID used for the radiography, it is preferable that the cassette ID should be read right before or right after the radiography. Further, in this embodiment, although ID reader 3f and radiographic table 6 are structured into a body, it may be possible to structure a handy type ID reader 3f so that the radiologist can operate the handy type ID reader 3f to read ID section C1 when taking radiographs.

Figure 13:
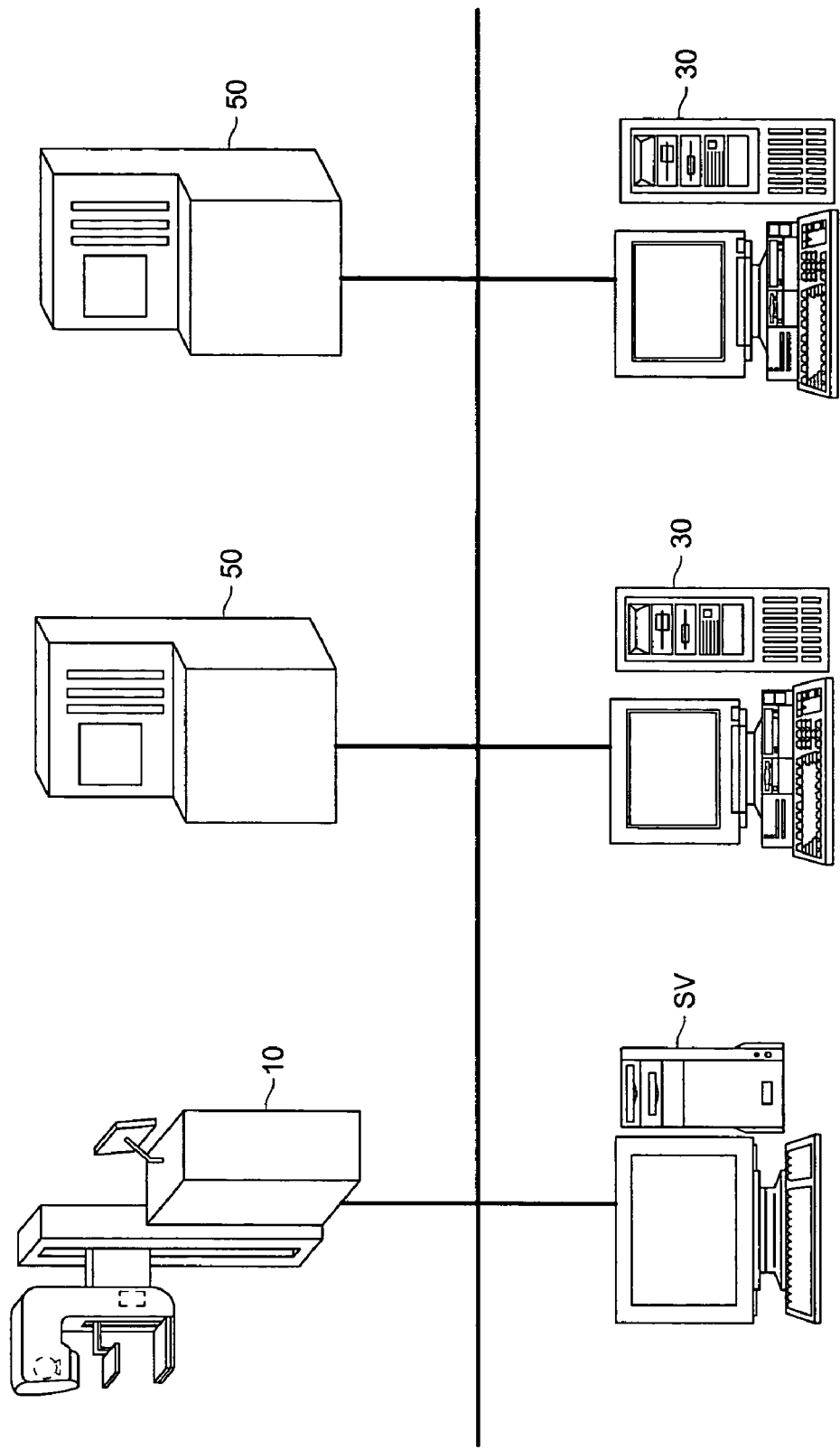
FIG. 13 shows a system configuration where a plurality of controllers 30 and a plurality of reading apparatuses 50(s) are connected.

In mammographic system 100 described above, although an example including one control apparatus 30 and one reading apparatus 50 is explained, as shown in FIG. 13, the present invention can be applied to a system configuration to which a plurality of control apparatuses 30(s) and a plurality of reading apparatuses 50(s) are connected through a network. In this case, since cassette registration can be conducted in an arbitrary control apparatus 30, a server SV for controlling the route to transmit the read mammographs read from cassette C by each reading apparatus 50 to a certain control apparatus 30, should be provided. When cassette registration is conducted, each control apparatus 30 transmits the registered ID and controller ID to identify each control apparatus 30 in which the cassette registration is conducted. Sever SV correlates cassette ID registered from each control apparatus 30, with controller ID of control apparatus 30 in which the cassette registration is conducted, and memorizes them. Each reading apparatus 50 issues an inquiry of destination of the mammograph based on the cassette ID when reading the cassette ID of cassette C to server SV, and server SV transmits controller ID corresponding to cassette ID which is inquired to reading apparatus 50 as a response. Reading apparatus 50 transmits the mammograph and cassette ID to control apparatus 30 of which controller ID is specified by server Sv.

Even though a plurality of reading apparatuses 50(s) and a plurality of control apparatuses 30(s) are provided, it is possible for each control apparatus 30 to control each reading apparatus 50 to correlate radiographic order information and radiography execution information with mammographs.

It is possible to modify a detailed configuration and detailed operation of mammographic system 100 being the first embodiment of the present invention without departing from the spirit and scope of the invention.

The Second Embodiment

In the second embodiment of the invention, a mammographic apparatus is arranged so that it transmits cassette identification information together with body part direction information as key information. In the control apparatus, radiography execution information and the cassette identification information are correlated to radiographic order information. Based on this correlation, mammographs, radiographic order information and radiography execution information can be correlated without conducting a cassette registration. Following is an explanation of the second embodiment of the invention.

The configuration of the second embodiment will be described.

Since the mammographic system of the second embodiment is the same configuration as mammographic system 100 of the first embodiment, the same code is attached to the same portion of the configuration and the illustration will be eliminated. Namely, mammographic system 100 of the second embodiment of the invention comprises mammographic apparatus 10, control apparatus 30 and reading apparatus 50.

Since the configuration of mammographic apparatus 10 is the same of the first embodiment (refer to FIGS. 2–7), the detail description will not be described here.

In mammographic apparatus of the second embodiment, radiography execution information is generated in controller 3a and body part direction determination is conducted by controller 3a based on a rotation angle of radiographic section 1 detected by angle detecting section 8. The determined body part direction information is included in radiography execution information as key information for correlating the radiography execution information with radiographic order information, and the radiography execution information including the key information and the cassette ID of a cassette, which is read when taking radiographs, are transmitter to control apparatus 30 by communication section 3e.

Since the configuration of control apparatus 30 is the same as the first embodiment (refer to FIGS. 8–9), it will not be described here.

In control apparatus 30 of the second embodiment, control section 31 correlates the radiography execution information with radiographic order information based on the body part direction information included in the radiography execution information transmitted from mammographic apparatus 10 and the body part direction information included in the radiographic order information memorized in memory 36, every time when taking radiographs. When a mammograph and cassette ID information are transmitted from reading apparatus 50, the mammograph transmitted from reading apparatus 50 and radiography execution information are correlated based on the received cassette ID and cassette ID included in radiography execution information correlated with radiographic order information. Namely, the mammograph is correlated with radiographic order information based on radiography execution information.

Reading apparatus 50 reads mammographs recorded on cassette C. Reading apparatus 50 comprises an image reading device, an identification information reader and a communication device, like the first embodiment. Mammographs and cassette ID are read from a cassette set in reading apparatus 50 by the identification information reader and the read mammographs and cassette ID information is transmitted to control apparatus 30 by the communication device.

The operation of mammographic system 100 of the second embodiment of the invention will be described. The second radiography process performed by mammographic system 100 will be described by referring to FIG. 14. As a base for the explanation, in this embodiment, it is assumed that since when taking radiographs of breast images, there is no case that the same radiograph is taken with the same portion direction, when a plurality of terms of radiographic order information is registered for a patient, each body part direction has a different body part direction from each other.

Figure 14:
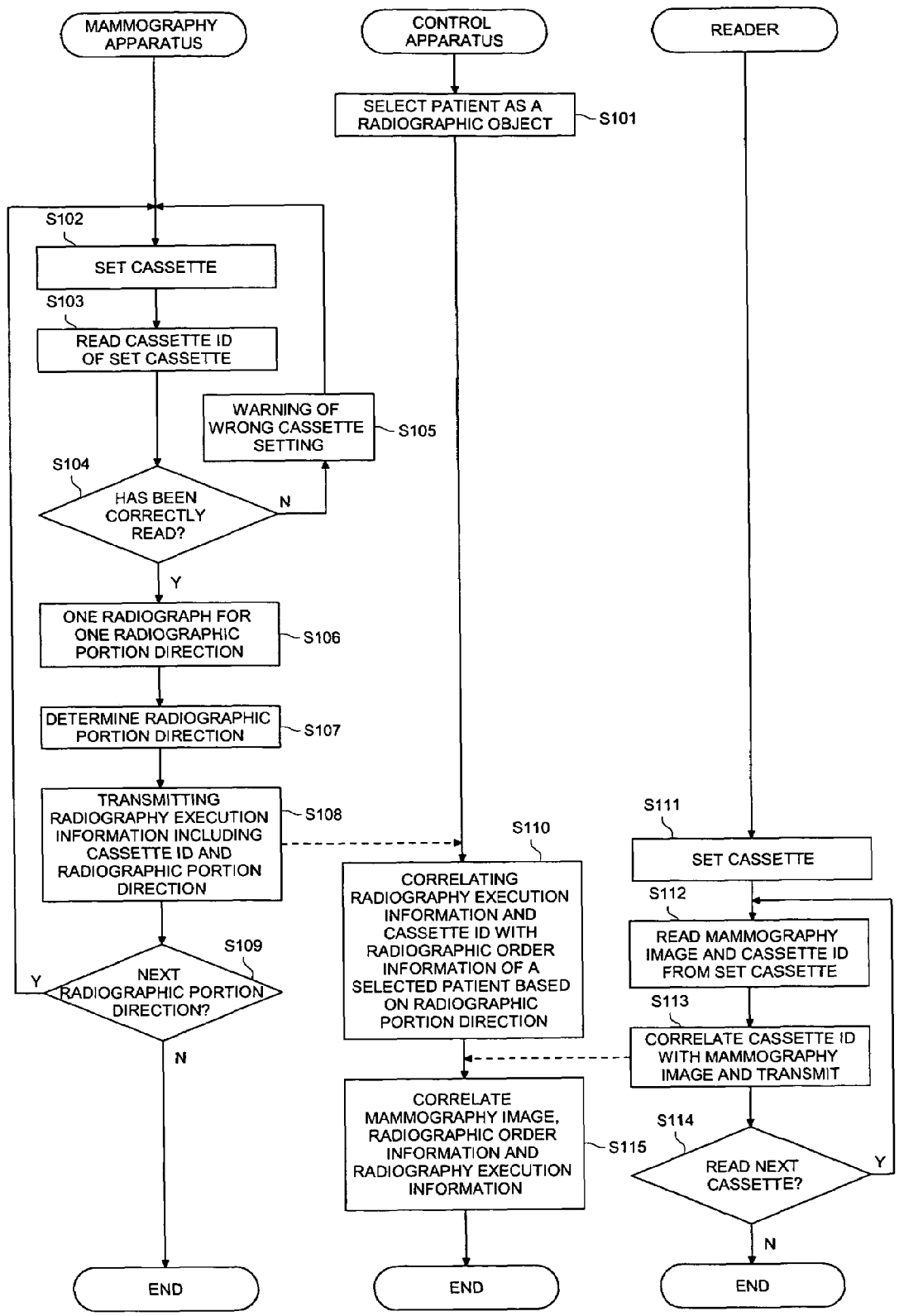
FIG. 14 is a flowchart of the second radiographic process executed in mammographic system 100 of the second embodiment of the present invention.

In the second radiographic process shown in FIG. 14, the list of patients to be radiographed is displayed in display section 33 of control apparatus 30 based on the radiographic order information stored in order file 361. When a radiologist selects and inputs a patient to be radiographed among the patient listed and displayed on the display section 33, then the list of the radiographic order information corresponding to the selected patients to be radiographed is displayed in control apparatus 30 (step S101).

When a radiologist confirms radiographic order information displayed on control apparatus 30, the radiologist moves to a radiography room where mammographic apparatus 10 is set, with a plurality of cassettes C and sets an arbitrary cassette C on radiographic table 6 of mammographic apparatus 10. The radiologist makes the patient being a radiographic object stand on a radiography position, and inputs a radiography start signal through input section 3b after adjusting the radiography portion and the radiography direction for radiography. In mammographic apparatus 10, cassette C has been set and the a radiography start signal have been inputted (step S102), cassette ID of cassette C which has been set is read (step S103) Then, in ID reader 3f determines whether cassette ID is correctly read (step S104).

As shown in FIGS. 11(b) and 11(c), when cassette C is wrongly inserted and ID reader 3f do not correctly read cassette ID (step S104; N), message announcing a read-error of cassette ID is displayed on display 3c, and warning that cassette C has been wrongly inserted (step S105). After the warning, the process returns to step S102 and insertion of cassette C is conducted again.

On the other hand, when cassette c is correctly inserted and cassette ID is correctly read by ID reader 3f (step S104; Y), in mammographic apparatus 10, X-rays are irradiated according to the radiography direction inputted from input section 3b and radiography is conducted. Namely, in one body part direction, one radiograph is taken (step S106). After the radiography, in mammographic apparatus 10, the body part direction is determined from the rotation angle of radiographic section 1 (step S107) and radiography execution information including cassette ID read by ID reader 3f is generated and transmitted to control apparatus 30 (step S108). Furthermore, in a CC radiography, L or R information could be added to the radiography execution information from the inputting section by the radiologist.

When all radiographs for one patient have not been taken and following body part direction is scheduled (step S109; Y); in mammographic apparatus 10, the process is returned to step S102; cassette C used for following radiography is set; and the radiography operation described above is repeated (step S102–S109). When all radiographs are taken (step S109; N), this process finishes.

In control apparatus 30, when the radiography execution information including cassette ID information and radiographic portion direction information from mammographic apparatus 10 are received, the radiography execution information is correlated to the radiographic order information based on the radiographic portion information included in the radiographic execution and the radiographic portion direction information included in the radiographic order information of a selected patient and memorized in order file 361 (step S110).

For example, as shown in FIG. 12, supposing that there are radiographic order information A (body part direction; RCC), radiographic order information B (body part direction; RM), radiographic order information C (body part direction; LCC) and radiographic order information D (body part direction; LM) for a selected one patient and radiography execution information W-Z which include each body part direction information is transmitted to control apparatus 30. In control apparatus 30, radiographic order information B is correlated with radiographic conduct information W; radiographic order information A is correlated with radiographic conduct information X; radiographic order information C is correlated with radiographic conduct information Y; and radiographic order information D is correlated with radiographic conduct information Z.

On the other hand, the radiologist carrying all cassette C used for the radiography moves to reading apparatus 50, sets one of cassette C into reading apparatus 50 and inputs reading instruction after finishing a plurality of radiographies for a patient. In reading apparatus 50, when cassette C is set (step S111), mammographs and cassette ID are read from the set cassette C (step S112) and cassette ID is correlated with the mammograph by writing the read cassette ID in a header area of the mammograph. The mammograph with which a cassette ID is correlated is transmitted to control apparatus 30 from reading apparatus 50 in the order by which the mammograph is read (step 113).

When reading all cassettes C for one patient has not finished and there is a next cassette to be read (step S114; Y), in reading apparatus 50, the process is returned to the process of steps S111–S113 and repeats the reading operations of next cassette C being set. When reading all cassettes C is finished (step S114; N), this process finishes.

In control apparatus 30, when mammograph is received from reading apparatus 50, it is stored into image database 362 and correlated with radiographic order information and radiography execution information based on cassette ID corresponding to the mammograph and cassette ID corresponding to radiographic order information (step S115). The radiographic order information and the radiography execution information correlated to the mammography are attached to the mammograph as additional information.

Figure 15:
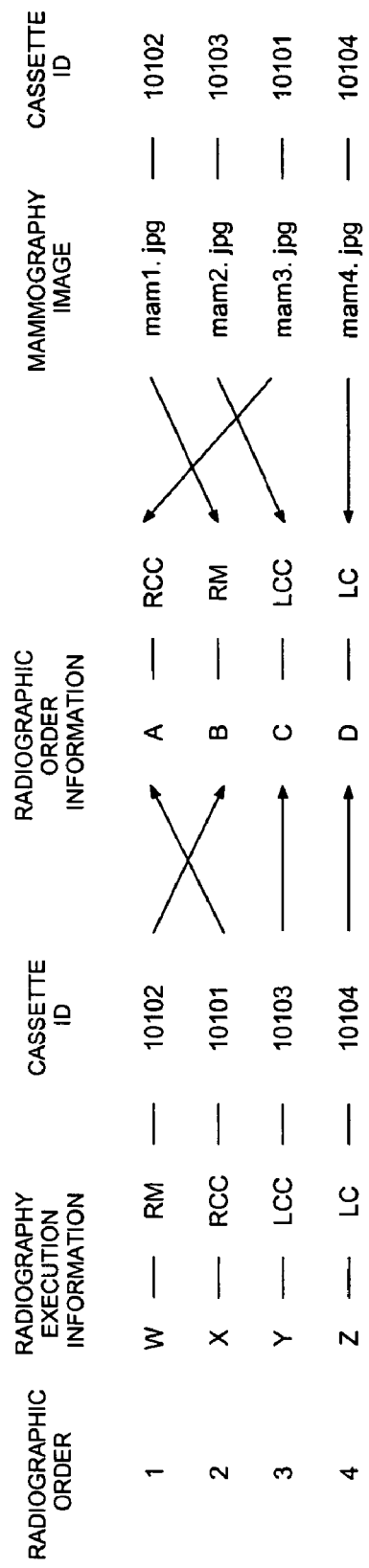
FIG. 15 shows a correlation between a mammograph and radiographic order information and the radiography execution information.

As shown in an example in FIG. 15, when cassette ID 10102 is correlated with mammograph data file mam1.jpg, cassette ID 10103 is correlated with mammograph mam2.jpg, cassette ID 10101 is correlated with mammograph mam3.jpg and cassette ID 10104 is correlated with mammograph mam4.jpg, radiographic order information B and radiography execution information W are correlated with mammograph mam1.jpg, radiographic order information C and radiography execution information Y are correlated with mammograph mam2.jpg, radiographic order information A and radiography execution information X are correlated with mammograph mam3.jpg and radiographic order information D and radiography execution information Z are correlated with mammograph mam4.jpg.

A radiologist returns to control apparatus 30 to operate it after finishing the read operation of cassette C with reading apparatus 50. When finishing the correlation operation of the mammograph, radiographic order information and radiography execution information in control apparatus 30, a confirmation screen for confirming the correlation between mammograph and radiographic order information and radiography execution information is displayed in display 33 and finishing the process.

The radiologist moves for taking radiographs of the next patient after confirming the correlation by the confirmation screen. In mammographic system 100, the first radiographic process described above is repeated again from step S101.

As described above, providing ID reader 3f for reading cassette ID in mammographic apparatus 10 and transmitting the read cassette ID together with radiography execution information to control apparatus 30 allow control apparatus 30 to automatically correlate a mammograph with radiographic order and radiography execution information based on cassette ID. Accordingly, the selection operation for selecting radiographic order information with which radiographic order information is correlated by the radiologist prior to the radiography can be eliminated and the efficiency of radiographic work can be improved.

When taking radiographs of breast images, since it is common to take a radiograph or a plurality of radiographs of each left and right breast with an up-down (CC) direction, an inside-outside direction and an oblique direction, at least two radiographs per a patient are obtained. Accordingly, by registering a patient to be a subject prior to the radiography, it becomes possible to continuously take a plurality of radiographs of the patient, which reduces the workload of the radiologist. Since the radiologist can complete the radiography with only one movement to a control apparatus, a mammographic apparatus and a reading apparatus during the radiography.

Further, it is not necessary to register cassette C to be used for radiography and it can reduce the workload of a radiologist. Since it is not necessary to memorize each relation of cassette ID and radiographic portion direction over the plurality of cassettes prior to the radiography or after the radiography, the efficiency of radiography work can be improved and miscorrelation is eliminated.

In mammographic apparatus 10, since radiographic table 6 is integrated with ID reader 3f and ID section C1 of cassette C is automatically read, the radiologist does not need to input cassette ID and it is not only convenient but also can prevent the radiologist from conducting a human error of the radiologist such as oblivion of inputting cassette ID. When cassette C has not been correctly set and the cassette ID cannot be correctly read, the warning is displayed. Accordingly, cassette miss-reading can be prevented and miss-radiography.

The contents of the description for the second embodiment of the invention is a preferable embodiment of the invention and not limited to this embodiment. Although it is desirable that with regard to read timing of the cassette ID in ID reader 3f, since it can warn of a reading error and can be made to reset with cassette C before photography, when it is not able to correctly read the cassette C before photography, as mentioned above, it may be read after the radiography. In either case, from the viewpoint for raising the certainty of cassette ID used for the radiography, it is preferable that the cassette ID should be read right before or right after the radiography. Further, in this embodiment, although ID reader 3f and radiographic table 6 are structured into a body, it may be possible to structure a handy type ID reader 3f so that the radiologist can operate the handy type ID reader 3f to read ID section C1 when taking radiographs.

In the second embodiment of the invention, as shown in FIG. 13, the present invention can be applied to a system configuration to which a plurality of control apparatuses 30(s) and a plurality of reading apparatuses 50(s) are connected through a network. In this case, since cassette registration can be conducted in an arbitrary control apparatus 30, a server SV for controlling the route to transmit the read mammographs read from cassette C by each reading apparatus 50 to a certain control apparatus 30, should be provided. In the second embodiment of the invention, since cassette registration is not conducted, each control apparatus 30 receives radiography execution information including cassette ID and body part direction information out of mammographic apparatus 10. When body part direction is correlated with radiographic order information based on the body part direction information, order ID in the correlated radiographic order information and cassette ID information included in the radiography execution information are correlated with control apparatus ID and it is transmitted to sever SV.

Server SV stores order ID and cassette ID and control apparatus ID received from each control apparatus 30. Each reading apparatus 50 inquires of destination of mammographs to server SV based on cassette ID of cassette C when reading the cassette ID and server SV transmits the control apparatus ID corresponding to cassette ID of which destination is inquired to reading apparatus 50 as a response. Reading apparatus 50 transmits the mammograph to control apparatus 50 whose control-apparatus ID is specified by server SV. As described above, even though a plurality of reading apparatuses 50(s) and a plurality of control apparatuses 30(s) are provided, radiographic order information and radiography execution information can be correlated with mammograph obtained based on the control of each reading apparatus 50 by each control apparatus 30.

In the case of a system configuration shown in FIG. 13, in order to specify the destination, which is one of plural control apparatuses 30(s), to which the radiography execution information generated by mammographic apparatus 10 is transmitted, mammographic apparatus 10 is arranged that mammographic apparatus 10 is connected to control apparatus 30 with one to one (1:1) to be able to communicate to predetermined control apparatus 30 among the plural control apparatuses 30(s). This one to one (1:1) relationship can be established by server SV as following. Server SV specifies a communication party between mammographic apparatus 10 and control apparatus 30. For example, when taking radiographs, control apparatus 30 issues request for taking radiographs to server SV and server SV specify control apparatus 30 which issued the request for taking radiographs as a destination of radiography execution information, and responds to mammographic apparatus 10. Mammographic apparatus 10 transmits radiography execution information including body part direction information and cassette ID information to control apparatus 30 specified as the one to one (1:1) relationship.

Or, the system configuration can be arranged so that mammographic apparatus 10 comprises a fist communication mode capable of communicating specified control apparatus 30 and a second communication mode capable of communicating arbitrary control apparatus 30. While radiography is not conducted, the second communication mode is set and mammographic apparatus 10 is set to communicate to arbitrary control apparatus 30. When any one of control apparatuses 30(S) issues request for taking radiography, mammographic apparatus 10 switches the communication mode to the first communication mode having one to one relationship, capable of communicating with control apparatus which issued the request. When finishing the radiography, the communication mode is switched back to the second communication mode.

In FIG. 13, a system including one mammographic apparatus 10 connected to a network is shown. However, a plurality of mammographic apparatuses 10(s) may be connected the network. In this case, in order to specify the target to which the radiography execution information is sent, each mammographic apparatus 10 are arranged to communicate to only predetermined and specified control apparatus 30. Or, it may be allowed that the relationship between mammographic apparatus 10 and control apparatus 30 being one to one (1:1) is arranged so that there is a plurality of combinations of the relationship in the system configuration. Or, as described above, server SV may conduct a communication control for changing a communication mode so that mammographic apparatus 10 which is specified to take radiographs and control apparatus 30 which has issued request for taking radiographs are arranged to establish the one to one (1:1) relationship. Instead of providing sever SV, the control function of server SV may be conducted by control apparatus 30.

Further, in the second embodiment of the invention, mammographic apparatus 10 comprises ID reader 3f as a identification information reader to read cassette ID. However, when mammographic apparatus 10 cannot provide ID reader 3f therein, as shown in FIG. 16(a), cassette ID reader 70 having an identification information reader, such as a barcode reader, to read cassette ID displayed in ID section C1 of cassette C may be connected to mammographic apparatus 10. A general purpose computer having CPU, RAM, storage, display and an input section may be used as cassette ID reader 70.

A radiography workflow in the system configuration will be described below by using an example where mammography of L-MLO (left breast, medio lateral oblique direction) and R-MLO (right breast, medio lateral oblique direction) are conducted.

1) A radiologist sets a control apparatus near a radiology room to display radiographic order information of a patient to be a subject to know the necessary number of cassette based on the displayed radiographic order information, then enters the radiology room.

2) After the radiologist has cassette ID reader 70 read cassette ID of cassette C to be used, sets cassette C on radiographic table 6, set radiographic section 1 of mammographic apparatus to L-MLO (left breast, oblique direction) and inputs radiographic section 1.

3) In cassette ID reader 70, read cassette ID is transmitted to mammographic apparatus 10. In mammographic apparatus 10, after finishing radiography based on a radiographic direction, body part direction is identified and radiography execution information including the identified body part direction is generated and transmitted to control apparatus together with cassette ID information transferred form cassette ID reader 70. In control apparatus 30, the radiography execution information and cassette ID are correlated to radiographic order information based on the body part direction (L-MLO) included in the received radiography execution information.

4) On the other hand, the radiologist set the cassette C onto radiographic table 6 after has cassette ID reader 70 read cassette C to be used for next time, set radiographic section 1 of mammographic apparatus 10 to R-MLO (right breast, oblique direction) and inputs the radiography direction.

5) In cassette ID reader 70, the same as item 3), cassette ID is transmitted to mammographic apparatus 10. In mammographic apparatus 10, after finishing the radiography conducted based on the radiographic direction, cassette ID information transmitted from cassette ID reader 70 is transmitted to control apparatus 30 together with radiography execution information including body part direction information (R-MLO).

6) The radiologist sets cassette C including mammographs of L-MLO and R-MLO in reading apparatus 50 in turn to read the images. In reading apparatus 50, cassette ID and mammographs are read from cassette C. The cassette ID is correlated with the read mammographs and transmitted.

7) In control apparatus 30, radiographic order information and radiography execution information are correlated with the mammographs based on cassette ID correlated with received mammographs As described above, since the radiologist allows the cassette ID reader to read cassette ID of cassette C to be used for radiography every time when taking a radiograph, cassette ID and radiography execution information can be correlated with radiographic order information in cassette ID reader 70 in every photography. Accordingly, after finishing the photography of one patient, mammographs, radiographic order information and radiography execution information are correlated each other based on cassette ID in control apparatus 30 by collectively loading the cassette c which the radiologist has used into reading apparatus 50.

As shown in FIG. 16(b), a system having cassette ID reader 70 provided between mammographic apparatus 10 and control apparatus 30 may be possible. In this case, the radiologist makes cassette ID reader 70 read cassette ID of cassette C every time when radiograph is taken. In mammographic system 100, radiography execution information including body part direction information from mammographic apparatus 10 is transmitted to cassette ID reader 70 in every radiography. In cassette ID reader 70, read cassette ID information is sent to control apparatus 30 together with radiography execution information including the body part information. Mammographs and cassette ID from reading apparatus 50 are transmitted to control apparatus 30. In control apparatus 30, mammographs, radiographic order information and radiography execution information are correlated each other base on body part direction information and cassette ID.

Figure 17:
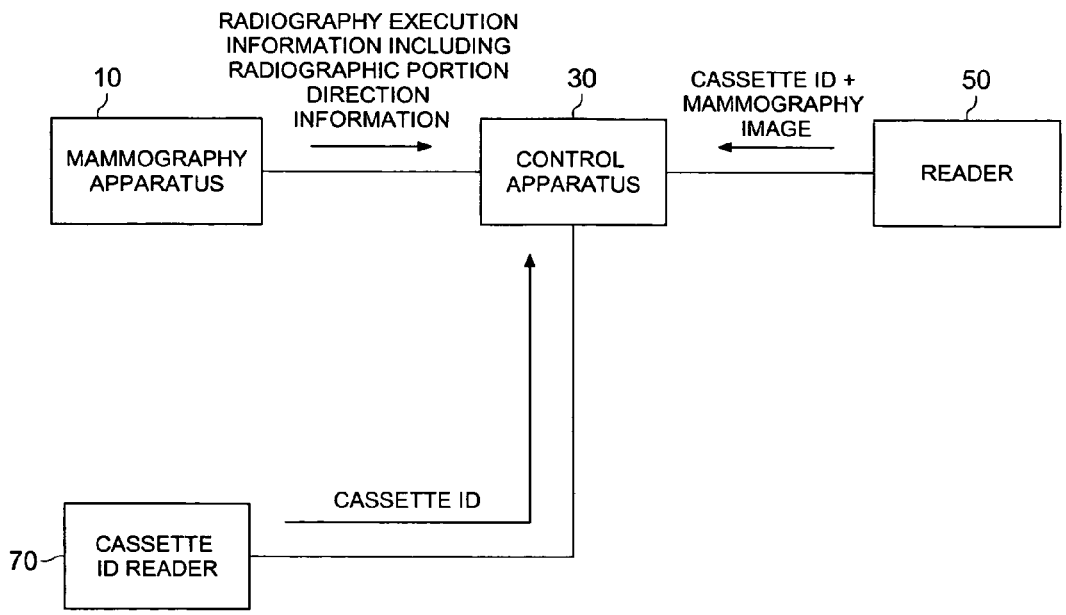
FIGS. 17(a) and 17(b) are system configurations of mammographic system 100 provided with cassette reader 70.
Figure 17:
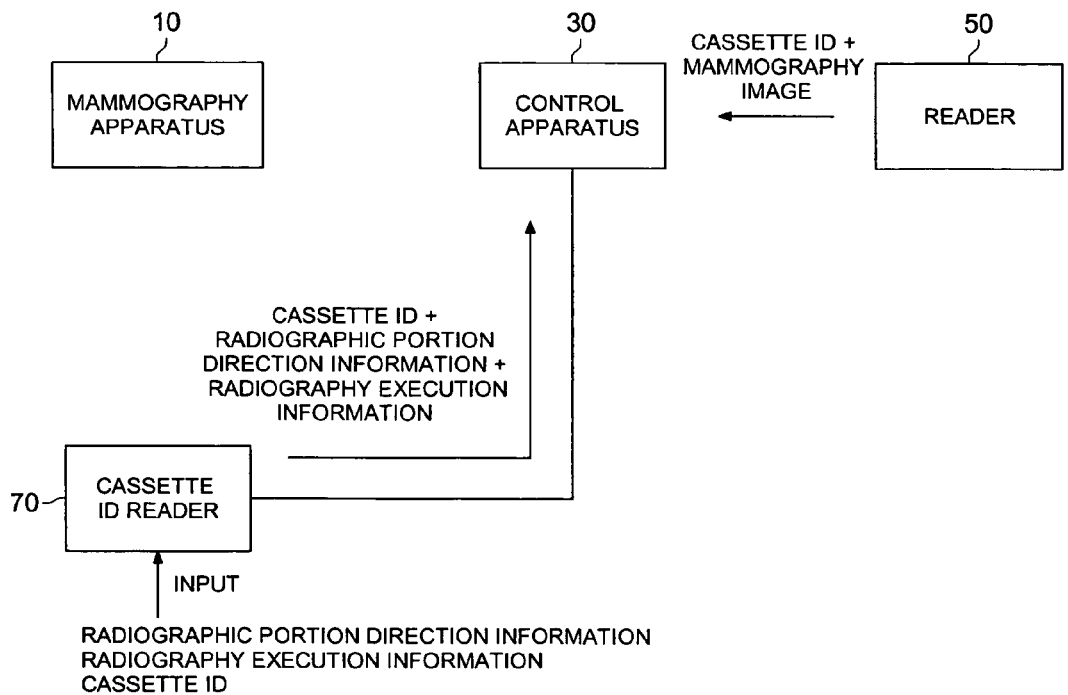

Further, as shown in FIG. 17(*a*), cassette ID reader 70 may be directly connected to control apparatus 30. In this case, the radiologist makes cassette ID reader read cassette ID of cassette C every time when radiography is conducted. In cassette ID reader 70, cassette ID is transmitted to control apparatus 30 just after the cassette ID is read. In mammographic apparatus 10, radiography execution information including body part direction information is transmitted to control apparatus 30 every time when a radiograph is taken. In control apparatus 30, since every time when radiograph y is performed, radiography execution information including body part direction information from mammographic apparatus 10 and cassette ID from cassette ID reader are received, the received radiography execution information and cassette ID information are correlated according to the order which they are received, and radiography execution information and cassette ID are correlated with radiographic order information based on body part direction information included in correlated radiographic execution information. Then, mammographs and cassette ID from reading apparatus 50 are received, radiographic order information and radiography execution information are correlated with the mammograph based on cassette ID.

As shown in FIG. 17(*b*), a system in which mammographic apparatus 10 is not connected to control apparatus 30 but only cassette ID reader 70 is connected to control apparatus 30 may be allowed. In this case, a radiologist inputs the radiography execution results of mammographic apparatus 10, which is radiography execution information into cassette ID reader 70. The same as the above, body part direction information is also inputted and at the same time, cassette ID of cassette C is read. In cassette ID reader 70, inputted body part direction information, radiography execution information and read cassette ID information are transmitted to control apparatus 30. When control apparatus 30 receives body part direction information, radiography execution information and cassette ID information from cassette ID 70 are received, mammographs, radiographic order information and radiography execution information are correlated each other based on body part direction information and cassette ID. In this system configuration, it is preferable that by setting cassette ID reader 70 and mammographic apparatus 10 in the same radiology room, radiologist does not need to move to input cassette C to reading apparatus 50 every time when taking a radiograph and/or does not need to memorize the radiographic order with respect to the cassette C to set the cassette in the radiographic order.

Figure 18:
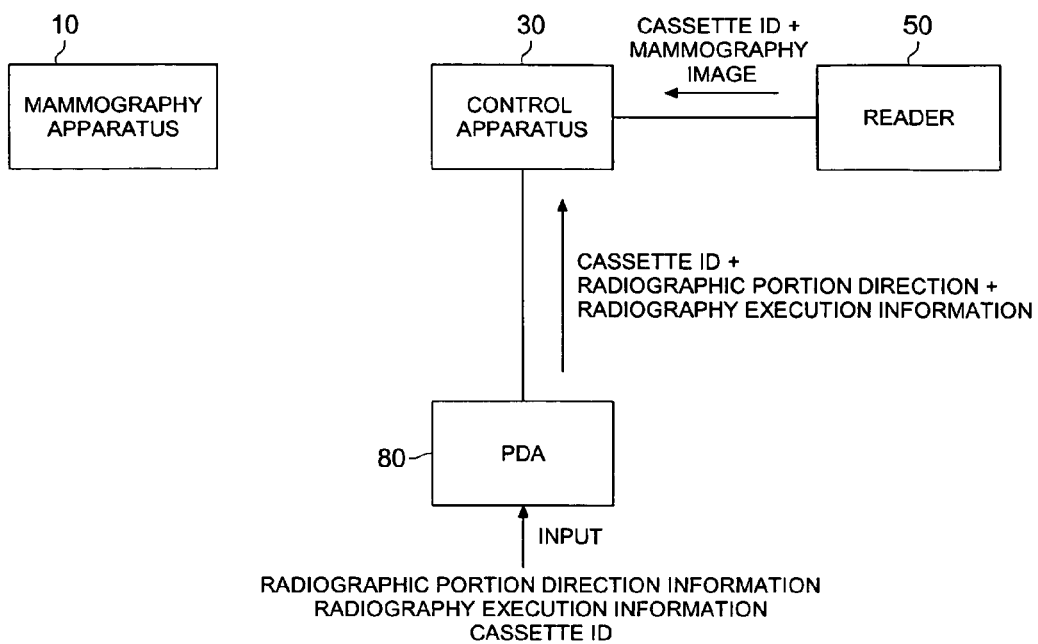
FIGS. 18(a) and 18(b) are system configurations of mammographic system 100 provided with PDA 80.
Figure 18:
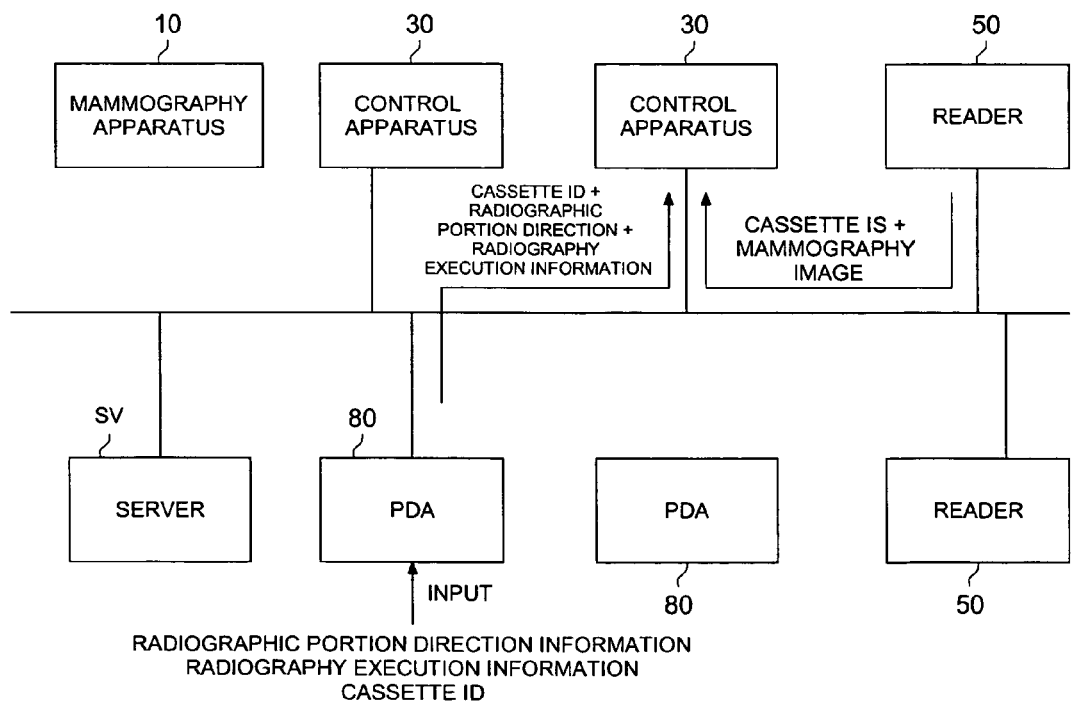
Figure 19:
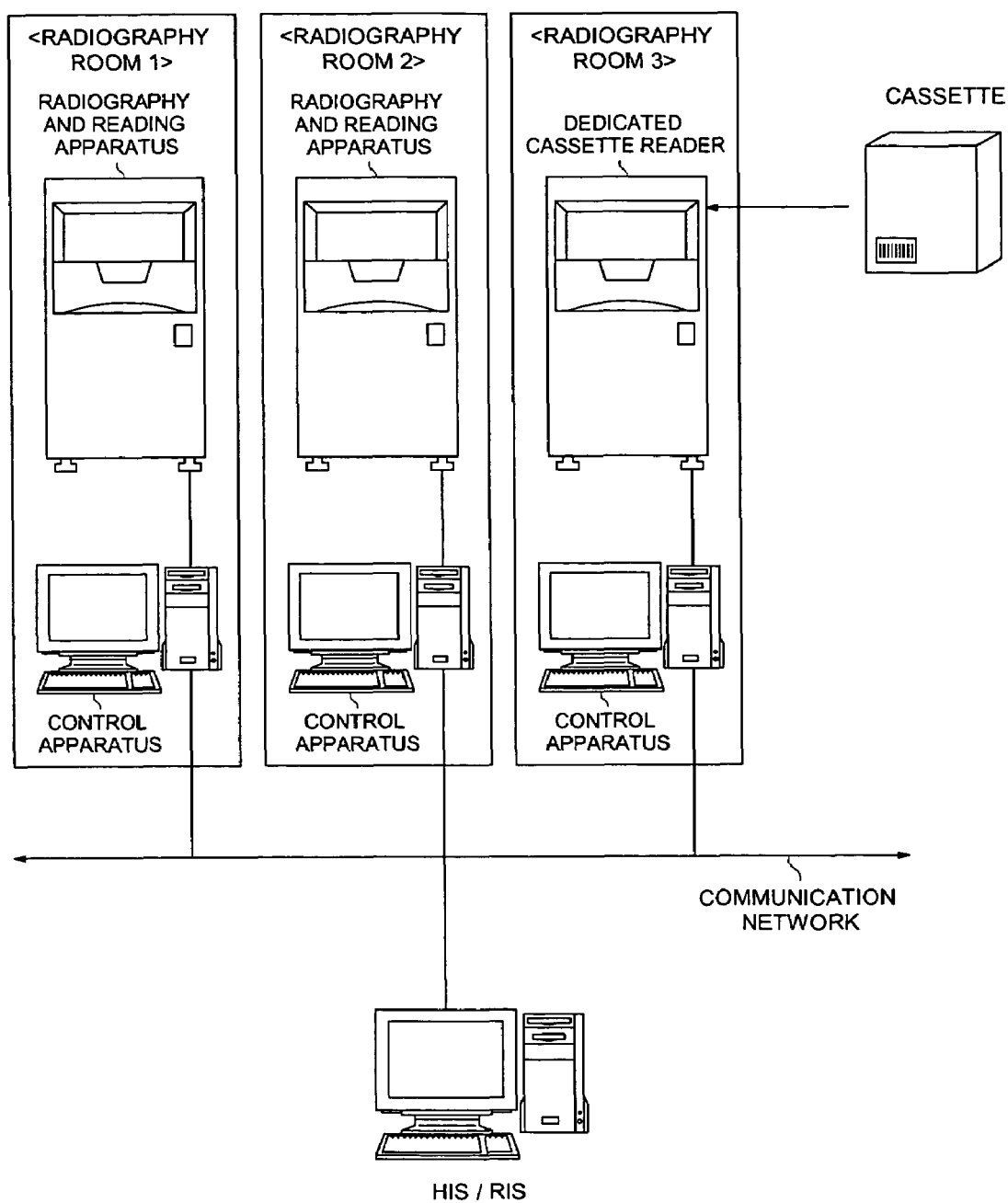
FIG. 19 is a system configuration of a conventional mammographic apparatus.

As shown in FIG. 18(*a*), a system including a specific control apparatus 30 to which PDA (Personal Digital Assistance) 80 capable of being transportable is connected for communication instead of cassette ID reader 70 may be allowed. In this case, a radiologist inputs body part direction information, radiography execution information and cassette ID information through PDA 80. PDA 80 transmits inputted body part direction information, radiography execution information and cassette ID information to the specific control apparatus 30 through a cradle (not shown). When control apparatus 30 receives body part direction information, radiography execution information and cassette ID information from PDA 80 and mammographs and cassette ID from reading apparatus 50, mammograph, radiographic order information and radiography execution information are correlated each other based on body part direction and cassette ID. According to this system configuration, since PDA is used it is convenient for a radiologist to conduct an input operation even though the radiologist is in a work.

As shown in FIG. 18(*b*), a system configuration including plural control apparatuses 30(*s*), reading apparatuses 50(*s*) and PDAs 80(*s*) connected through network N may be allowed. In this case, since arbitrary control apparatus 30 can be accessed from PDA 80, an IP address of each control apparatus 30 which can be accessible is registered into PDA 80 in advance so that the radiologist can specify to which control apparatus 30 cassette ID, body part direction information and radiography execution information are transmitted. As described above, a server SV may be provide to control to which control apparatus 30 the mammograph read by each reading apparatus 50 is transmitted. PDA 80 transmits inputted body part direction information, radiography execution information and cassette ID information to control apparatus specified by a radiologist.

As shown above, although, plural control apparatuses 30(*s*), reading apparatuses 50(*s*) and PDAs 80(*s*) are provided in a system, each control apparatus 30 can correlate radiographic order information and radiographic execution information with mammographs obtained from each reading apparatus 50 based on body part direction and cassette ID information received from each PDA 80.

Figure 16:
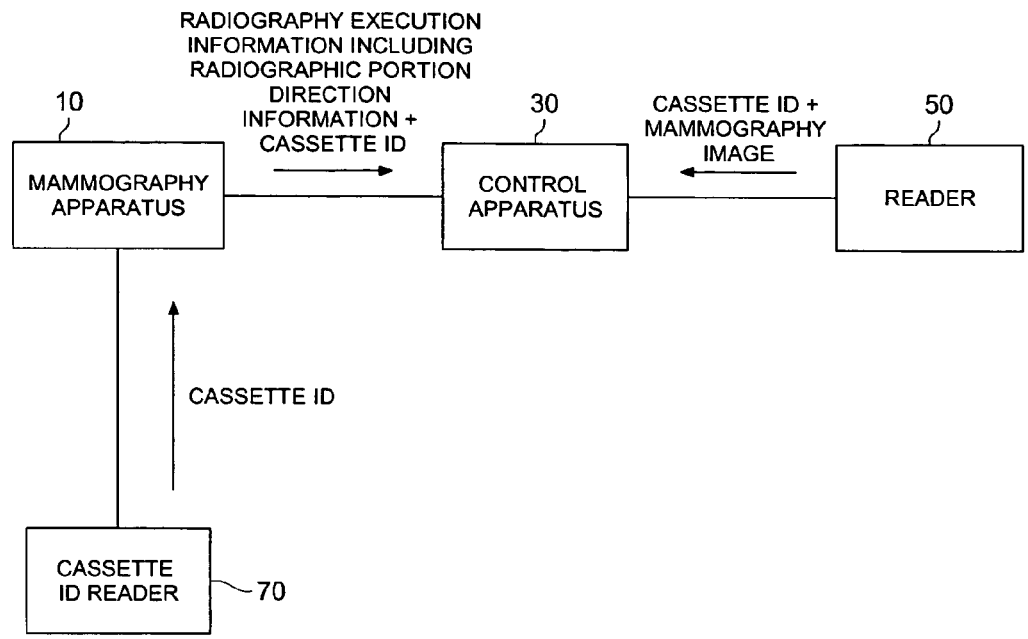
FIGS. 16(a) and 16(b) are system configurations of mammographic system 100 provided with cassette reader 70.
Figure 16:
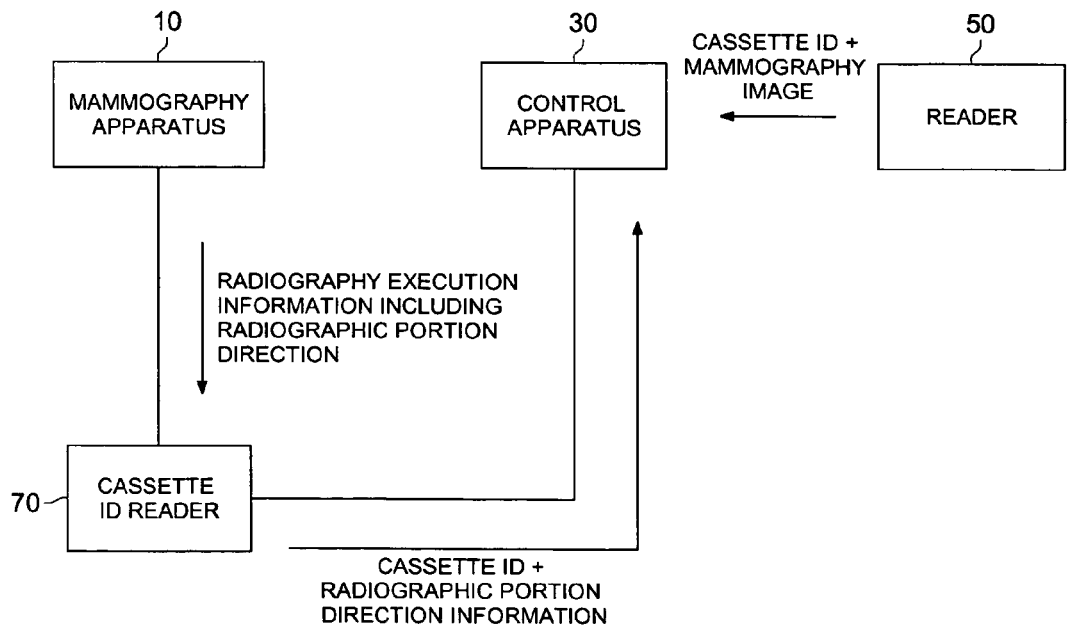

Further, even in the first embodiment of the invention, when ID reader 3*f* cannot be provided in mammographic apparatus 10, the system configurations shown in FIGS. 16–18 can be applied. Accordingly, in control apparatus 30, radiographic order information and radiography execution information can be correlated with mammographs received from reading apparatus 50.

In the second embodiment, obtained data of mammography is automatically correlated to the key information, which means body part (right or left breast) and mammography direction (CC or MLO etc).

So, each obtained mammography could be automatically processed in configurations and allocated in such a format as FIG-2D of U.S. Pat. No. 5,212,637 for viewing according to the key information.

Furthermore, before allocation, such a processing as extracting ROI (region of interest), tone characteristic and enhancement so on, is applicable in each suitable manner according to the key information.

Of course, after allocation, aforementioned processing could be applicable.

According to the another aspect of the present invention, since the radiographic order information and the radiography execution information are correlated to the mammographs based on the cassette ID, it becomes possible to correlate the radiographic order information to the radiography execution information as additional information with regard to the mammographs and based on the additional information, it becomes possible to confirm radiography execution information of the mammographs later. Also it becomes possible to conduct precise image management.

According to another aspect of the present invention, since the cassette ID information is read while the cassette is set, cassette ID information can be securely read when taking radiographs.

According to the another aspect of the present invention, since the cassette ID information is automatically read while the cassette is set in a radiographic table, workload of the radiologist, such as inputting cassette ID information by the radiologist is not necessary. Accordingly it is not only convenient but also it prevents the radiologist from causing a mistake based on a human error, such as forgetting input-operation.

According to the another aspect of the present invention, the cassette ID information is read right before the radiography or right after the radiography, the miss usage of a cassette can be prevented and the cassette ID information of the cassette used for the radiography can be securely read.

According to another aspect of the present invention, even a plurality of reading apparatuses is set, the radiographic order information and the radiography execution information are correlated to the mammographs which are obtained from each reading apparatus based on the cassette ID information.

According to another aspect of the present invention, in mammography where a plurality of mammographs with different radiographic body parts and different body part directions is conducted, it becomes possible to allow the radiographic body part and/or the radiographic direction which are/is useful information for correlating the radiographic order information with the radiography execution information to be key information.

According to another aspect of the present invention, since when mammography is conducted for a patient for one time for each right breast and left beast, or a plurality of mammographs with a plurality of radiographic directions is conducted for each right breast and left breast, it is common that the mammography is conducted on a right breast and a left breast in turn, the mammographs, the radiographic order information and the radiography execution information are correlated each other based on only right and left information. Accordingly, it becomes possible to improve the radiographic work efficiency especially in mammography where a plurality of radiographs with different radiographic body parts and different radiographic directions is conducted many times.

According to the another aspect of the present invention, since the cassette ID information is read while the cassette is set in the mammographic apparatus, the cassette ID information of the cassette used when taking radiographs can be securely read.

According to the another aspect of the present invention, since the cassette ID information is automatically read while the cassette is set in a radiograph table, workload of the radiologist, such as inputting cassette ID information by the radiologist is not necessary. Accordingly, it is not only convenient but also it prevents the radiologist from causing a mistake based on a human error, such as forgetting input-operation.

According to another aspect of the present invention, the cassette ID information is read right before the radiography or right after the radiography, the miss usage of a cassette can be prevented and the cassette ID information of the cassette used for the radiography can be securely read.

The detail configurations and operations of the first and second embodiments of the invention may be changed and modified without departing from the scope and spirit of the present invention.

What is claimed is:

1. A mammographic system, comprising:
   at least one mammographic apparatus for taking a mammograph of a subject by irradiating X-rays onto a breast and for recording the mammograph onto a recording medium in a cassette;
   at least one reading apparatus for reading the mammograph out of the cassette; and
   at least one control apparatus for obtaining the mammograph, the control apparatus being connected with the mammographic apparatus and the reading apparatus through a communication section,
   the mammographic apparatus having
      a first identification information reader for reading cassette identification information of the cassette used for taking the mammograph and
      a communication section for transmitting radiography execution information including the cassette identification information which has been read by the first identification information reader,
   wherein the control apparatus comprises
   a memory section for storing radiographic order information,
   an input section for inputting the cassette identification information to be used for taking the mammograph, and
   a controlling section for correlating the cassette identification information inputted by the input section with the radiographic order information and storing correlation in the memory section, and correlating the radiography execution information with radiographic order information based on the cassette identification information included in the radiography executing information transmitted from the mammographic apparatus and the cassette identification information included in the radiographic order information which has been stored in the memory section.

2. The mammographic system of claim 1,
   wherein the reading apparatus comprises a second identification information reader for reading the cassette identification information when reading the mammograph out of the cassette, and the controlling section of the control apparatus correlates the read mammograph, the radiographic order information and the radiography execution information each other based on the cassette identification information registered with the radiographic order information and the cassette identification information correlated to the mammograph transmitted from the reading apparatus.

3. The mammographic system of claim 2,
   wherein the control apparatus is connected to a plurality of reading apparatuses through the communication section and the control apparatus controls the plurality of reading apparatuses, and correlates the radiographic order information and the radiography execution information with each mammograph obtained by controlling the plurality of reading apparatuses.

4. The mammographic system of claim 3, further comprising:
   a plurality of control apparatuses, each of which controls the plurality of reading apparatuses to correlate the radiographic order information and the radiography execution information with each obtained mammograph.

5. The mammographic system of claim 1,
wherein the first identification information reader of the mammographic apparatus reads the cassette identification information while the cassette is set in the mammographic apparatus.

6. The mammographic system of claim 5 wherein the first identification information reader of the mammographic apparatus is integrated with a radiographic table on which the cassette is set, and automatically reads the cassette identification information set on the radiographic table.

7. The mammographic system of claim 1,
wherein the first identification information reader in the mammographic apparatus reads the cassette identification information just before or just after a radiography.

8. A mammographic system, comprising:
a mammographic apparatus for taking a mammograph of a subject by irradiating X-rays onto a breast and for recording the mammograph onto a recording medium in a cassette;
at least one reading apparatus for reading the mammograph out of the cassette; and
at least one control apparatus for obtaining the mammograph which has been read out of the cassette, wherein the mammographic apparatus comprises
a first identification information reader for reading an cassette identification information to be used for taking the mammograph,
an information generating section for generating radiography execution information including key information which correlates the radiography execution information with radiographic order information, and
a first communication section for transmitting the radiography execution information including the key information generated by the information generating section and the cassette identification information which has been read by the first identification information reader to the control apparatus every time when taking the mammograph, wherein the reading apparatus comprises
a second identification information reader for reading the cassette identification information when the mammograph is read out of the cassette, and
a second communication section for transmitting the mammograph and the cassette identification read by the second identification information reader information to the control apparatus, wherein the control apparatus comprises
a memory section for storing the radiographic order information including the key information, and
a controlling section for correlating the radiography execution information including the cassette identification information received from the mammographic apparatus with the radiographic order information based on the key information included in the radiography execution information and the key information included in the radiographic order information stored in the memory section, and correlating the mammograph with the radiographic order information based on the cassette identification information correlated with the radiographic order information by the key information and the cassette identification information transmitted from the reading apparatus with the mammograph.

9. The mammographic system of claim 8,
wherein the key information is at least one of radiographic body part information and radiographic direction information.

10. The mammographic system of claim 8,
wherein the key information is information showing that a radiographic body part is a right breast or a left breast.

11. A method of controlling for a mammographic system including
a mammographic apparatus for taking a mammograph of a subject by irradiating X-rays onto a breast and for recording the mammograph onto a recording medium in a cassette,
a reading apparatus for reading the mammograph out of the cassette, and
a control apparatus for obtaining the mammograph, the control apparatus being connected with the mammographic apparatus and the reading apparatus through a network, the method of controlling the mammographic system comprising the steps of:
selecting radiographic order information in the control apparatus;
inputting the cassette identification information to be used for the selected radiographic order information by using an input section in the control apparatus;
correlating the cassette identification information inputted by the input section with the selected radiographic order information and storing correlation in the memory section in the control apparatus;
reading the cassette identification information of the cassette used for taking the mammograph by using a first identification information reader of the mammographic apparatus;
generating radiography execution information including the cassette identification information read by the first identification information reader;
transmitting the radiography execution information including the cassette identification information from the mammographic apparatus to the control apparatus;
correlating the cassette identification information inputted by the input section with the radiographic order information and storing correlation in the memory section; and
correlating the radiography execution information with radiographic order information based on the cassette identification information included in the radiography executing information transmitted from the mammographic apparatus and the cassette identification information included in the radiographic order information which has been stored in the memory section.

12. A method of controlling for a mammographic system including
a mammographic section for taking a mammograph of a subject by irradiating X-rays onto a breast and for recording the mammograph onto a recording medium in a cassette,
a reading section for reading the mammograph out of the cassette, and
a control section for obtaining the mammograph which has been read out of the cassette, the method of controlling the mammographic system, comprising the step of:
selecting and storing a radiographic order information including key information in the control section
reading an cassette identification information to be used for taking the mammograph by a first identification information reader of the mammographic section;
generating radiography execution information including key information which correlates the radiography execution information with radiographic order information, in an information generating section of the mammographic section;

transmitting both of the radiography execution information including the key information generated by the information generating section and the cassette identification information read by the first identification information reader to the control section in each taking the mammography;

reading the cassette identification information by a second identification information reader of the reading section when the mammograph is read out of the cassette;

transmitting both of the read mammograph and the cassette identification read by the second identification information reader information to the control section;

correlating the radiography execution information including the cassette identification information received from the mammographic section with the radiographic order information based on the key information included in the radiography execution information and the key information included in the radiographic order information stored in the memory section; and correlating the mammograph with the radiographic order information based on the cassette identification information correlated with the radiographic order information by the key information and the cassette identification information transmitted from the reading section with the mammograph.

13. The method of controlling for the mammographic system of claim 12, wherein the key information includes an information of at least one of a body part and mammographic direction.

14. The method of controlling for the mammographic system of claim 13 further comprising:

allocating the mammography in a predetermined format according to the key information in the control section.

15. The method of controlling for the mammographic system of claim 13, further comprising:

processing the data of the mammography for viewing according to the key information in the control section.

* * * * *